United States Patent [19]

Wong et al.

[11] Patent Number: 5,416,087
[45] Date of Patent: May 16, 1995

[54] BIS-BENZO, CYCLOHEPTA PIPERIDYLIDENE, PIPERIDINE AND PIPERAZINE COMPOUNDS, COMPOSITIONS AND METHODS OF USE

[76] Inventors: Jesse K. Wong, 547 Andress Ter., Union, N.J. 07083; John J. Piwinski, 19 Pitman Rd., Parsippany, N.J. 07054; Michael J. Green, 43 Meadow Run Dr., Skillman, N.J. 08558

[21] Appl. No.: 39,072
[22] PCT Filed: Oct. 8, 1991
[86] PCT No.: PCT/US91/07170
§ 371 Date: Apr. 7, 1993
§ 102(e) Date: Apr. 7, 1993
[87] PCT Pub. No.: WO92/06970
PCT Pub. Date: Apr. 30, 1992

Related U.S. Application Data

[63] Continuation-in-part of Ser. No. 595,329, Oct. 10, 1990, abandoned.

[51] Int. Cl.[6] .............. A61K 31/44; A61K 31/495; C07D 401/12; C07D 401/06
[52] U.S. Cl. .................. 514/252; 514/254; 514/318; 544/360; 544/361; 546/193; 546/194
[58] Field of Search ............. 544/360, 361; 546/193, 546/194; 514/252, 254, 318

[56] References Cited

U.S. PATENT DOCUMENTS

| | | | |
|---|---|---|---|
| 3,326,924 | 6/1967 | Villani | 260/293 |
| 3,370,058 | 2/1968 | Judd et al. | 540/587 |
| 3,717,647 | 2/1973 | Villani | . |
| 4,282,233 | 8/1981 | Villani | . |
| 4,308,207 | 12/1981 | Hunziker et al. | 540/587 |
| 4,355,036 | 10/1982 | Villani | . |
| 4,826,853 | 5/1989 | Piwinski et al. | 514/290 |
| 5,089,496 | 2/1992 | Piwinski et al. | 544/361 |
| 5,104,876 | 4/1992 | Piwinski et al. | 544/361 |
| 5,151,423 | 9/1992 | Piwinski et al. | 544/361 |

FOREIGN PATENT DOCUMENTS

| | | |
|---|---|---|
| 0042544 | 4/1984 | European Pat. Off. . |
| 0371805 | 6/1990 | European Pat. Off. . |
| 03138 | 5/1988 | WIPO . |
| 10363 | 11/1989 | WIPO . |
| 00293 | 1/1992 | WIPO . |

OTHER PUBLICATIONS

Arzneim.-Forsch/Drug Research 36 II No. 9, pp. 1311-1314 (1986).
Journal of Medicinal Chemistry, vol. 15, No. 7, pp. 750-754 (1972).

Primary Examiner—Cecilia Tsang
Attorney, Agent, or Firm—Edward H. Mazer

[57] ABSTRACT

Bis-benzo cyclohepta piperidine, piperidylidene and piperazine compounds of the general formula,

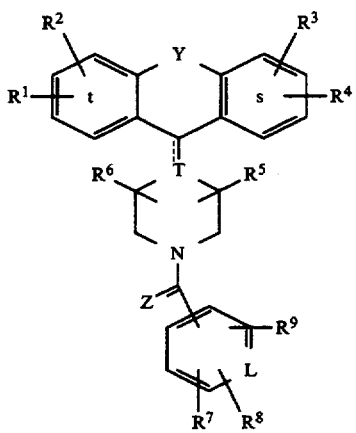

and pharmaceutically acceptable salts thereof are disclosed, which possess anti-allergic and/or anti-inflammatory activity. Methods for preparing and using the compounds are also described.

24 Claims, No Drawings

BIS-BENZO, CYCLOHEPTA PIPERIDYLIDENE, PIPERIDINE AND PIPERAZINE COMPOUNDS, COMPOSITIONS AND METHODS OF USE

The present application is the U.S. national application corresponding to International Application No. PCT/US91/07170, filed Oct. 8, 1991 and designating the U.S., which PCT application is in turn a continuation-in-part of U.S. application Ser. No. 07/595,329, filed Oct. 10, 1990, now abandoned, the benefit of which applications are claimed pursuant to the provisions of 35 U.S.C. §§120,363 and 365(C).

BACKGROUND OF THE INVENTION

The present invention relates to bis-benzo cyclohepta piperidine, piperidylidene and piperazine compounds and to pharmaceutical compositions and methods of using such compounds.

U.S. Pat. Nos. 3,326,924, 3,717,647 and 4,282,233, European published Application No. 0042544, Villani et al., *Journal of Medicinal Chemistry*, Vol. 15, No. 7, pp 750–754 (1972) and *Arzn. Forsh* 36 1311–1314 (1986) describe certain 11-(4-piperidylidene)-5H-benzo[5,6]cyclohepta[1,2-b]pyridines as antihistamines. U.S. Pat. No. 4,355,036 describes certain N-substituted piperidylidene compounds.

WO 88/03138 discloses compounds of the formula

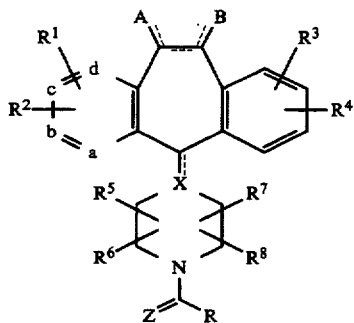

or a pharmaceutically acceptable salt or solvate thereof, wherein:
one of a, b, c and d represents N or $NR^9$ where $R^9$ is O, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, $-CF_3$, $-OR^{10}$, $-COR^{10}$, $-SR^{10}$, $-N(R^{10})_2$, $-NO_2$, $-OC(O)R^{10}$, $-CO_2R^{10}$, $-OCO_2R^{11}$, alkynyl, alkenyl or alkyl, which alkyl or alkenyl group may be substituted with halo, $-OR^{10}$ or $-CO_2R^{10}$;

$R^3$ and $R^4$ may be the same or different and each independently represents H, any of the substituents of $R^1$ and $R^2$, or $R^3$ and $R^4$ together may represent a saturated or unsaturated fused $C_5$–$C_7$ ring;

$R^5$, $R^6$, $R^7$ and $R^8$ each independently represent H, $-CF_3$, alkyl or aryl, which alkyl or aryl may be substituted with $-OR^{10}$, $-SR^{10}$, $-N(R^{10})_2$, $-NO_2$, $-COR^{10}$, $-OCOR^{10}$, $-OCO_2R^{11}$, $-CO_2R^{10}$, $-OPO_3R^{10}$ or one of $R^5$, $R^6$, $R^7$ and $R^8$ may be taken in combination with R as defined below to represent $-(CH_2)_r-$ where r is 1 to 4 which may be substituted with lower alkyl, lower alkoxy, $-CF_3$ or aryl;

$R^{10}$ represents H, alkyl or aryl;
$R^{11}$ represents alkyl or aryl;
X represents

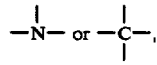

which C may contain an optional double bond to carbon atom 11;

the dotted line between carbon atoms 5 and 6 represents an optional double bond, such that when a double bond is present, A and B independently represent H, $-R^{10}$, $-OR^{11}$ or $-OC(O)R^{10}$, and when no double bond is present between carbon atoms 5 and 6, A and B each independently represent:

$H_2$ and $-(OR^{10})_2$;
alkyl and H;
(alkyl)$_2$;
$-H$, and $OC(O)R^{10}$;
$-H$ and $-OR^{10}$;
=O
aryl and H; or
$=NOR^{10}$ and $-O-(CH_2)_p-O-$;

where p is 2, 3 or 4 and $R^{10}$ is as previously defined;
Z represents O, S or $H_2$ such that
(a) when Z is O, R may be taken in combination with $R^5$, $R^6$, $R^7$ or $R^8$ as defined above, or R represents H, aryl, alkyl, $-SR^{11}$, $-N(R^{10})_2$, cycloalkyl, alkenyl, alkynyl or $-D$ wherein $-D$ represents heterocycloalkyl,

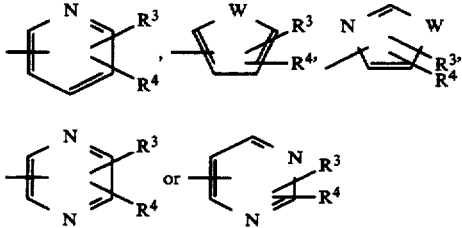

wherein $R^3$ and $R^4$ are as previously defined and W is O, S or $NR^{10}$ wherein $R^{10}$ is as defined above,
said cycloalkyl, alkyl, alkenyl and alkynyl being optionally substituted with from 1–3 groups selected from $-$halo, $-CON(R^{10})$ $-$aryl, $-CO_2R^{10}$, $-OR^{12}$, $-SR^{12}$, $-N(R^{10})_2$, $-N(R^{10})COR^{10}$, $-COR^{12}$, $-NO_2$ or $-D$, wherein $-D$ and $R^{10}$ are as defined above and $R^{12}$ represents $R^{10}$, $-(CH_2)_mOR^{10}$ or $-(CH_2)_qCOR^{10}$ wherein $R^{10}$ is as previously defined, m is 1 to 4 and q is 0 to 4, said alkenyl and alkynyl R groups not containing $-OH$, $-SH$ or $-N(R^{10})_2$ on a carbon containing a double or triple bond respectively
(b) when Z represents S, R represents in addition to those alkanediyl R groups above, aryloxy or alkoxy; and
(c) when Z represents $H_2$, R represents $-COOR^{10}$, $-E-COOR^{10}$ or $-E-OR^{12}$ where E is alkanediyl which may be substituted with $-OR^{10}$, $-SR^{10}$, $-N(R^{10})_2$ or $-D$ where D, $R^{10}$ and $R^{12}$ are as previously defined. These compounds are disclosed as being useful in the treatment of allergy and inflammation.

SUMMARY OF THE INVENTION

We have now unexpectedly found that compounds having the structural formula I below provide surprisingly good activity as PAF antagonists and as antihistamines. In particular, we have discovered such characteristics in compounds represented by the structural formula I

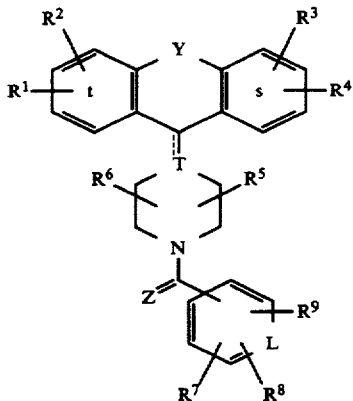

or a pharmaceutically acceptable salt or solvate thereof, wherein:

L represents N or $N^+O^-$;
Z represents O or S;
Y represents —$(C(R^a)_2)_m$—X—$(C(R^a)_2)_n$— or

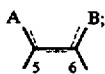

m and n are integers 0, 1, 2 or 3 such that the sum of m plus n equals 0 to 3;
when m plus n equals 1, X represents —O—, —S(O)$_e$— where e is 0, 1 or 2, —$NR^{14}$—, —C(O)NR$^{14}$—, —$NR^{14}$C(O)—, —C(S)NR$^{14}$—, —$NR^{14}$C(S)—, —$CO_2$— or —$O_2C$—, where $R^{14}$ is as defined below;
when m plus n equals 2, X represents —O—, —S(O)$_e$— where e is 0, 1 or 2, or —$NR^{14}$;
when m plus n equals 3, then X equals a direct bond
when m plus n equals 0, X can be any substituent as defined for m plus n equalling 1 and X can also be a direct bond, cyclopropylene or propenylene
each $R^a$ may be the same or different and each independently represents H, or $C_1$-$C_6$ lower alkyl;
the dotted line between the indicated carbon atoms 5 and 6 represents an optional double bond, such that when a double bond is present, A and B each independently represent —$R^{11}$, —$OR^{13}$, —halo or —$OC(O)R^{11}$, and when no double bond is present between carbon atoms 5 and 6, A and B each independently represent $H_2$, —$(OR^{13})_2$, (alkyl and H), (alkyl)$_2$, (—H and —$OC(O)R^{11}$), (H and —$OR^{11}$), =O or =$NOR^{14}$;
$R^1$, $R^2$, $R^3$, and $R^4$ may be the same or different and each independently represents —H, —halo, —$CF_3$, —$OR^{11}$, —C(=O)$R^{11}$, $SR^{11}$, —S(O)$_eR^{13}$ where e is 1 or 2, —$N(R^{11})_2$, —$NO_2$, —OC(=O)$R^{11}$, —$CO_2R^{11}$, —$OCO_2R^{13}$, $NR^{11}C(=O)R^{11}$, —CN, —CON($R^{11}$)$_2$, —alkyl, —aryl, —alkenyl or —alkynyl, which alkyl group may be substituted with —$OR^{11}$, —$SR^{11}$, —$N(R^{11})_2$ or —$CO_2R^{11}$ and which alkenyl group may be substituted with halo, —$OR^{13}$ or —$CO_2R^{11}$;

in addition, $R^1$ and $R^2$ may together form a benzene ring fused to the ring t and/or $R^3$ and $R^4$ may together form a benzene ring fused to the ring s;
$R^5$ and $R^6$ each independently represents H, alkyl or aryl, which alkyl may be substituted with —$OR^{11}$, —$SR^{11}$ or —$N(R^{11})_2$;
in addition, $R^5$ may be combined with $R^6$ to represent =O or =S;
$R^7$, $R^8$ and $R^9$ each independently represents H, halo, —$CF_3$, —$OR^{11}$, —C(O)$R^{11}$, $SR^{11}$, —S(O)$_eR^{13}$ where e is 1 or 2, —$N(R^{11})_2$, —$NO_2$, —$CO_2R^{11}$, —$OCO_2R^{13}$, $OCOR^{11}$, —CN, —CON($R^{11}$)$_2$, —$NR^{11}COR^{11}$, alkyl, aryl, alkenyl or alkynyl, which alkyl group may be substituted with —$OR^{11}$, —$SR^{11}$, —$N(R^{11})_2$, or —$CO_2R^{11}$ and which alkenyl group may be substituted with halo, —$OR^{13}$ or —$CO_2R^{11}$;
each $R^{11}$ independently represents H, alkyl or aryl;
each $R^{13}$ independently represents alkyl or aryl;
each $R^{14}$ independently represents H or alkyl;
T represents

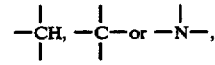

with the dotted line attached to T representing a double bond when T is

and being absent when T is

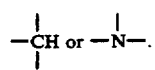

A more preferred embodiment of the present invention comprises compounds of the generalized structure

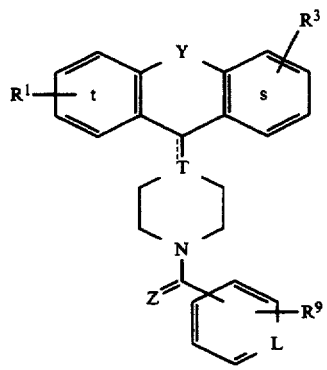

or a pharmaceutically acceptable salt or solvate thereof, wherein:

L represents N or N→O;
the dotted line represents an optional double bond;
Z represents O or S;
Y represents —CH=CH—, —CH₂—CH₂—, —X—, —CH₂—X—, —X—CH₂— or —(CH₂)₃—, wherein X represents —O—, —S— or —NR¹⁴—;
R¹, R³ and R⁹ may be the same or different and each independently represents H, halo, —CF₃, —OR¹¹, —N(R¹¹)₂, —alkyl, —alkenyl or —alkynyl; R⁹ may also be —SR¹¹;
T represents

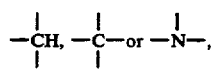

with the dotted line attached to T representing a double bond when T is

and being absent when T is

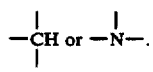

Particularly preferred compounds include the following:

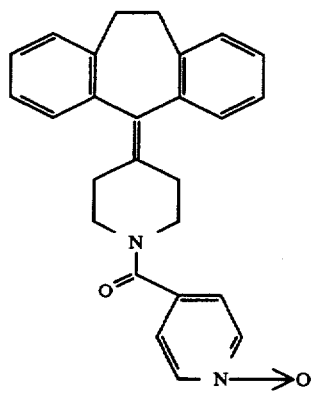

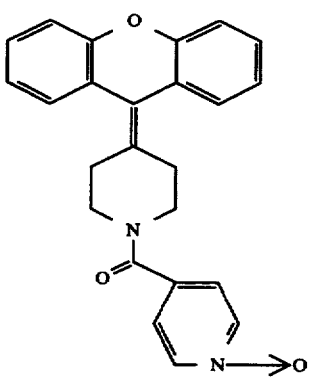

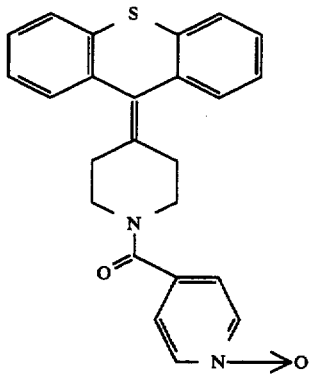

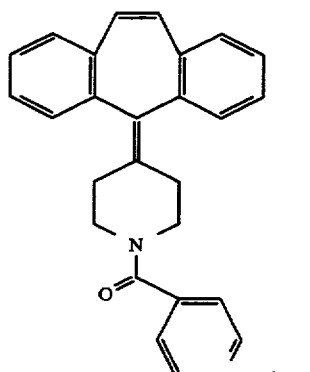

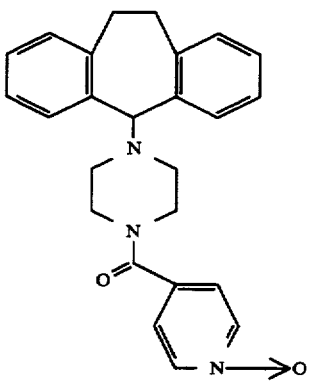

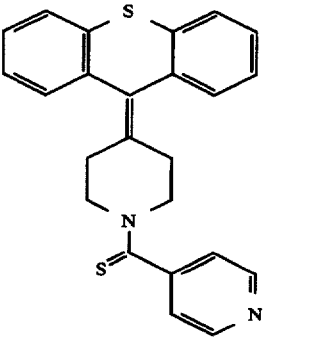

-continued

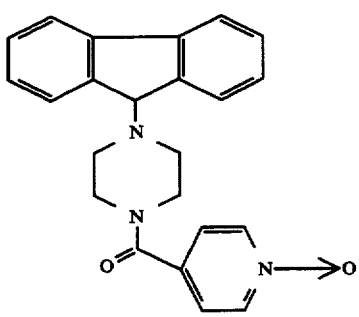

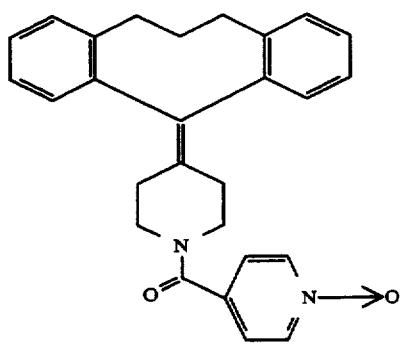

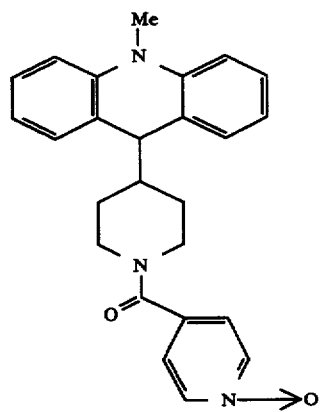

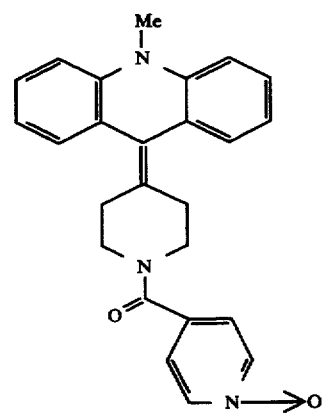

-continued

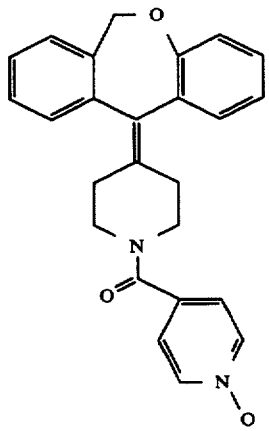

The present invention also preferably is directed at a method for treating an allergic reaction in a mammal comprising administering to a mammal an antiallergic effective amount of a compound of formula I.

The present invention also is directed at a method for treating inflammation in a mammal comprising administering to the mammal an antiinflammatory effective amount of a compound of formula I.

This invention also is directed at a pharmaceutical composition comprising a compound of formula I and a pharmaceutically acceptable carrier.

The present invention also is directed at a method for preparing a pharmaceutical composition comprising admixing a compound of formula I with a pharmaceutically acceptable carrier.

The present invention also is directed at a method for preparing a compound of formula I

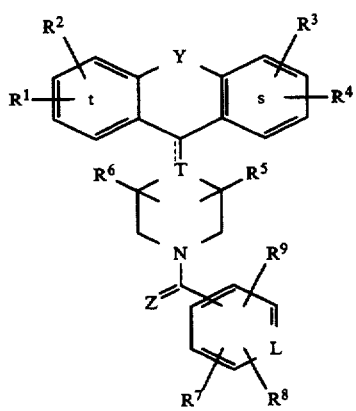

or a pharmaceutically acceptable salt or solvate thereof, comprising:

A. Reacting a compound of the formula II with a compound of formula III.

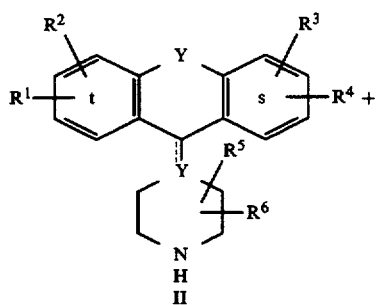

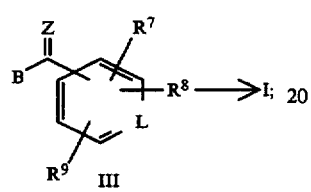

B. Where T represents nitrogen reacting a compound of formula XVII with a compound of formula VII;

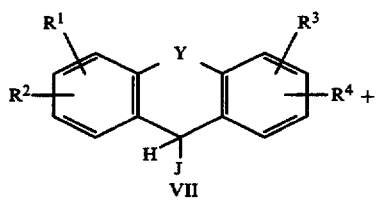

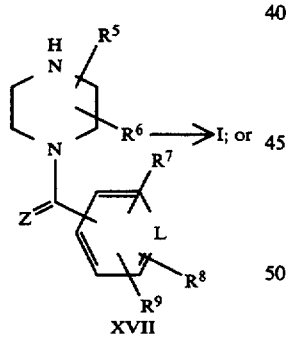

C. Where T represents nitrogen, reacting a compound of formula IX with a compound of formula XVII

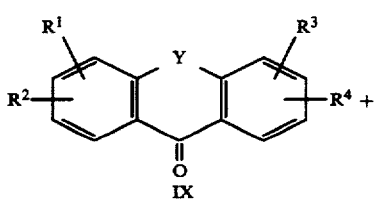

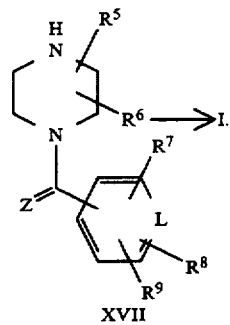

D. Where L represents nitrogen, reacting a compound of formula V with a compound of formula IIIa to provide formula I where L is nitrogen (L=N)

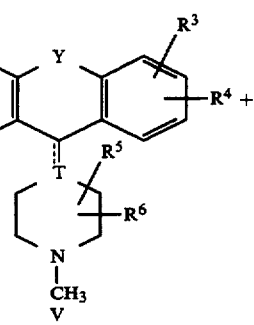

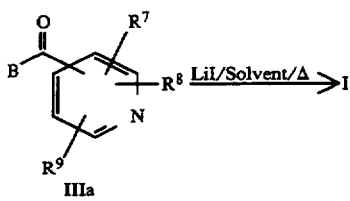

E. The compounds of formula I where L is nitrogen (L=N) can be oxidized to provide formula I where L is N-oxide (L=N—O).

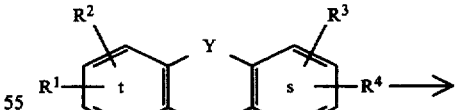

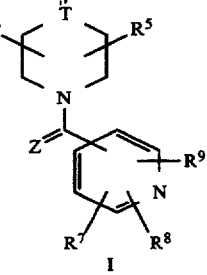

-continued

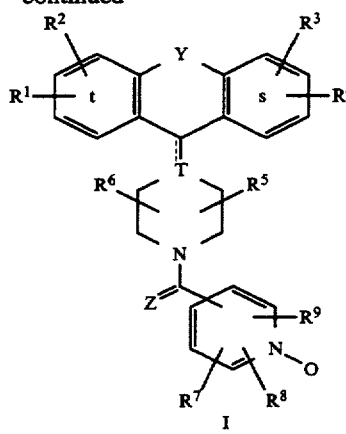

I

DETAILED DESCRIPTION OF THE INVENTION

Certain compounds of the invention may exist in different isomeric (e.g., enantiomers and diastereoisomers) as well as conformational forms. The invention contemplates all such isomers both in pure form and in admixture, including racemic mixtures. Enol forms are also included. For example, hydroxy substituted pyridinyl groups can also exists in their keto form:

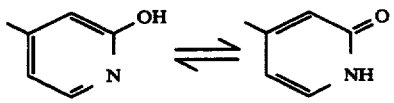

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the benzene ring structures of formula I may contain one or more substituents $R^1$, $R^2$, $R^3$ and $R^4$. In compounds where there is more than one such substituent, they may be the same or different. Thus compounds having combinations of such substituents are within the scope of the invention. Also, the lines drawn into the rings from the $R^1$, $R^2$, $R^3$ and $R^4$ groups indicate that such groups may be attached at any of the available positions. For example, the $R^1$ and $R^2$ groups may be attached to a carbon atom at the 1, 2, 3 or 4 positions while the $R^3$ and $R^4$ groups may be attached at any of the 7, 8, 9 or 10 positions.

$R^5$ and $R^6$ are attached to the piperidyl, piperidylidenyl or piperazinyl ring. As such they may be the same or different. The variables $R^5$ and $R^6$ in addition to representing H, may represent variables attached to the same or different carbon atoms in said ring. For example, when $R^5$ and $R^6$ are combined to represent =O or =S, they are attached to the same carbon atom.

The N-oxides are illustrated herein using the terms NO, N→O, N—O and $N^+O^-$. All are considered equivalent as used herein.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acids and bases are intended to be pharmaceutically acceptable salts within the scope of the invention and all acid and base salts are considered equivalent to the free forms of the corresponding compounds for purposes of the invention.

As used herein, the following terms are used as defined below unless otherwise indicated:

alkanediyl—represents a divalent, straight or branched hydrocarbon chain having from 1 to 6 carbon atoms, the two available bonds being from the same or different carbon atoms thereof, e.g., contains from one to twenty carbon atoms, preferably one to six carbon atoms;

cycloalkyl—represents saturated carbocyclic rings branched or unbranched of from 3 to 20 carbon atoms, preferably 3 to 7 carbon atoms;

alkenyl—represents straight and branched carbon chains having at least one carbon to carbon double bond and containing from 2 to 12 carbon atoms, preferably from 3 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_p$R$^a$ [wherein p is 0, 1 or 2 and R$^a$ is alkyl or aryl], —CF$_3$, amino, alkylamino, dialkylamino, —COOR$^{13}$ or —NO$_2$;

substituted phenyl—represents a phenyl group in which 1 to 3 hydrogen atoms thereof are replaced by the same or different substituents independently chosen from halo, alkyl, hydroxy, alkoxy, phenoxy, cyano, cycloalkyl, alkenyloxy, alkynyloxy, —SH, —S(O)$_p$R$^a$ [wherein p is 0, 1 or 2 and R$^a$ is alkyl or aryl], —CF$_3$, amino, alkylamino, dialkylamino, —COOR$^{13}$ or —NO$_2$; and halo—represents fluoro, chloro, bromo and iodo.

The following processes may be employed to produce compounds of general structural formula I.

A.

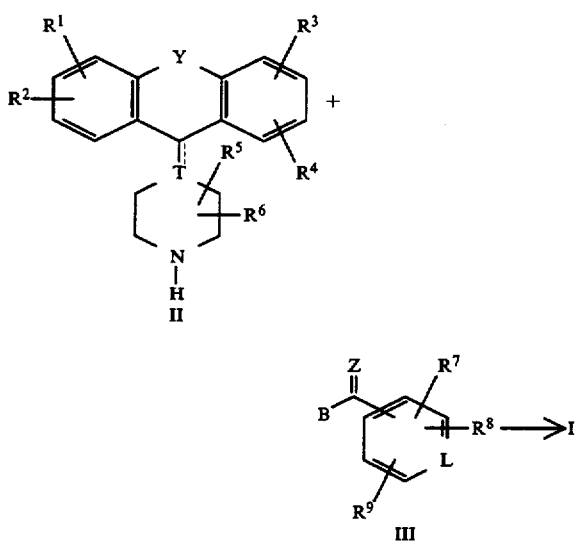

1. A compound of general formula II may be reacted with compound III in the presence of a base to produce compounds of general structural formula I. The reaction is usually conducted in an inert solvent such as THF or CH$_2$Cl$_2$ at suitable temperature. Representative examples of appropriate bases are pyridine and Et$_3$N, although in some cases a base is not necessary. B designates a suitable leaving group. For example, if Z is O or S, a compound of formula type III may be an acyl halide (e.g. B=halo), or an acyl anhydride

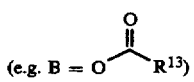

2. Alternatively, if the leaving group B is hydroxy, a coupling reagent may be employed to form compound I. Examples of coupling agents include N, N'-dicyclohexylcarbodiimide (DCC), carbonyldiimidazole (CDI), and 1-(3-dimethylaminopropyl)-3-ethylcarbodiimide hydrochloride (DEC). This is the preferred method that was used to make most of the compounds of the invention.
3. The leaving group may also be alkoxy, in which case the compounds of formula I may be produced by refluxing a compound of formula II with an excess of compound of formula III.
4. A method of making compounds of formula I where Z represents sulfur, comprises reacting a compound of formula I where Z is oxygen with P$_2$S$_5$, Lawesson's reagent, or another reagent capable of introducing sulfur in place of oxygen. The reaction may take place at elevated temperature in pyridine, toluene or other suitable solvents.

In this and other reactions, numerous conversions of a compound of formula I (Z=O) to another compound of formula I (Z=S) are possible.

B. Certain compounds of Formula I where T is nitrogen can also be prepared by alkylation of a compound of Formula XVII with a compound of Formula VII where J is a suitable leaving group such as a halide (e.g. J=Cl, Br, I) or other leaving group (e.g. tosyloxy or mesyloxy).

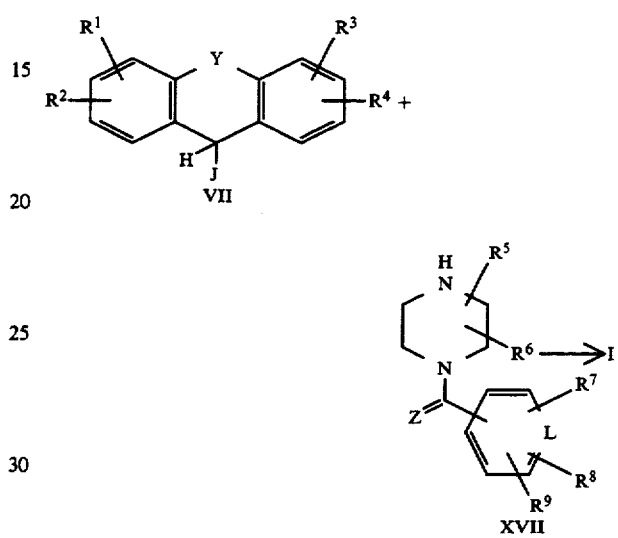

The reaction can be conducted in an inert solvent such as tetrahydrofuran or toluene, typically at a temperature range of ambient to reflux depending on the solvent of choice. A suitable base can be added such as triethylamine or potassium carbonate, although the reaction may proceed without it.

C. An alternative route for generating a compound of the invention Formula I where T is nitrogen may be by reductive amination of compound Formula IX with a compound of Formula XVII.

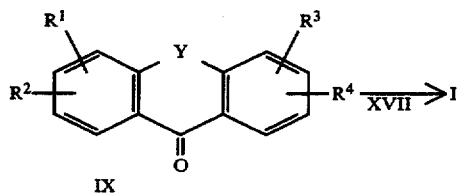

The reaction is typically carried out in a polar solvent such as an alcohol (e.g. methanol or ethanol) optionally in the presence of a water scavenger, such as 3A molecular sieves. The presence of a reducing agent such as NaCNBH$_3$ or H$_2$/Pd-C is necessary for reduction of the intermediate Schiff base. Temperatures for the reaction are typically held between 0°–100° C. depending on the solvent employed.

D. Compounds of formula I where L=N may be prepared directly by reacting a compound of formula V with a compound of formula IIIa.

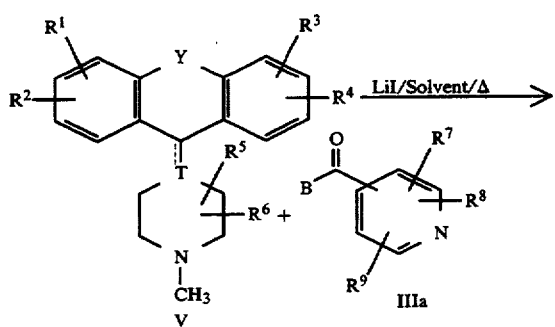

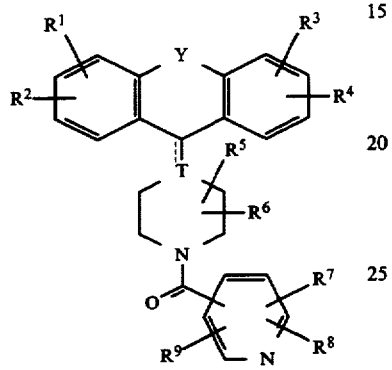

Preferably, the reaction is run in the presence of an appropriate nucleophile (e.g. LiI, etc) in an insert solvent (e.g. toluene, dioxane or xylenes). B is a suitable leaving group such as halo or OC(O)R' where R' can be alkyl, aryl or halogenated alkyl. An appropriate base may be added, and heating is usually required. Typically, a temperature ranging from 50°-300° C. (preferably 100°-175° C.) is utilized depending on the boiling point of the solvent.

E. The compound of formula I where L is nitrogen (L=N) can be oxidized to provide compounds of formula I where L is N-oxide (L=N→O), This process can be accomplished with an appropriate oxidizing agent in an inert solvent such as meta-chloroperbenzoic acid (MCPBA) in methylene chloride or hydrogen peroxide in acetic acid. The reaction is usually conducted from approximately −15° C. to reflux. This method is limited to compounds where T is C and where there is no nitrogen in the tricyclic moiety.

An intermediate compound of Formula XVIII can be prepared by coupling a compound of the Formula III with a compound of the Formula VIII.

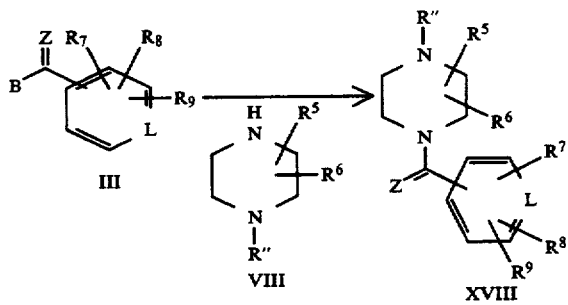

This can be accomplished by using coupling agent such as 1-(3-dimethylaminopropyl)-3-ethylcarbodii-mide hydrochloride (DEC) where B of Formula III is an hydroxyl group or by direct acylation in the presence of a base where B of Formula III is a good leaving group (e.g. B=halogen, tosyloxy, mesyloxy, etc). When R'' is hydrogen, the compound of Formula XVII is the same as compound of Formula XVIII. However, if R'' is a carbamate then the carbamate must be subsequently removed in order to provide compound XVII.

Compounds of general formula II are prepared by removal of the carbamoyl moiety (COOR' where R' can be for example alkyl, aryl or halogenated alkyl) from the corresponding carbamate IV via either acid (HCl/H₂O/reflux)

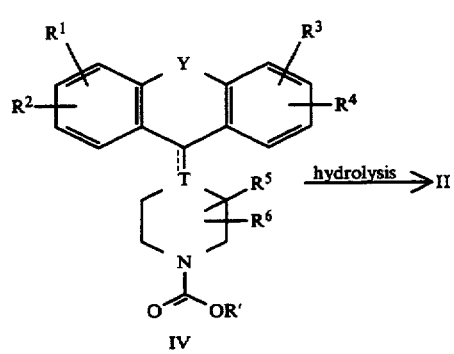

or base (KOH/H₂O/reflux) hydrolysis. Depending the nature of the carbamate, other methods can be employed, such as metal (Zn/AcOH for R'=CH₂CCl₃) reduction or an organometallic reagent (e.g. CH₃Li/THF for R'=alkyl) etc. to form the compounds of formula II.

Compounds of formula IV may be prepared from the N-alkyl (preferably N-methyl) compound shown as formula V below in the manner disclosed in U.S. Pat. Nos. 4,282,233, and 4,335,036 and in WO 88/03138. For example, the compound of formula V can be reacted with ethylchloroformate in an inert solvent such as toluene at a suitable temperature, e.g., 50° to 100° C. to form a compound of formula IV where R' is ethyl.

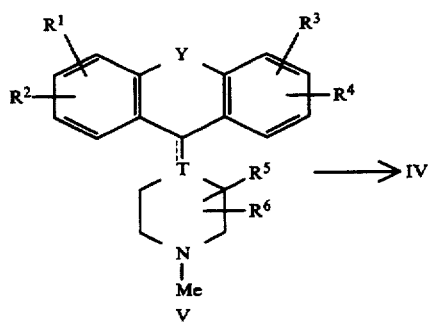

It also will be apparent to one skilled in the art that there are other methods for converting a compound of formula V to compound II. For example, treatment of a compound of formula V with BrCN via von Braun reaction conditions would provide nitrile VI as illustrated below. Subsequent hydrolysis of the nitrile VI under either aqueous basic or acidic conditions will produce a compound of formula II.

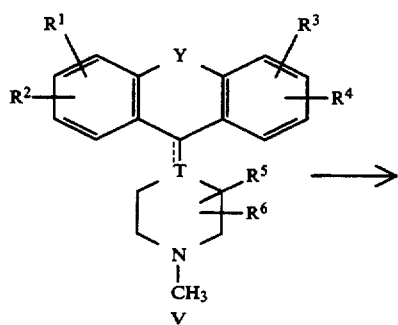

V

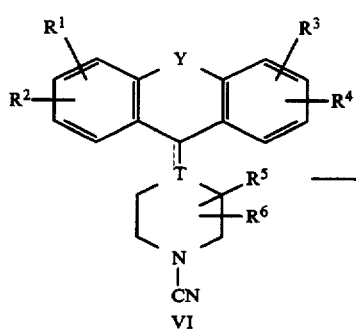

VI

PREPARATION OF PIPERAZINE ANALOGS

Compounds of the general Formulae IIa and Va below where T=N

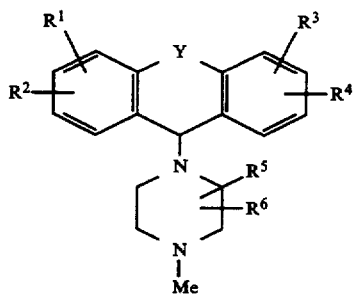

Va

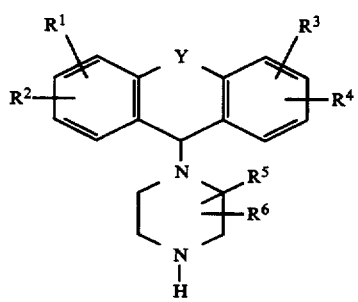

IIa may be produced by one of several methods disclosed generally the following patent publications: U.S. Pat. No. 4,616,023; BE 707523; WO 88/03138; and WO 87/07894. They are best prepared via alkylation of the appropriately substituted piperazine compound VIII (R″=H, Me) with the appropriately substituted bis-aryl compound VII. (J=halo, tosyl, mesyl or other leaving group). The reaction is usually conducted in an inert solvent such as THF or $CH_2Cl_2$ at a suitable temperature usually at reflux, although lower temperature can be employed. An appropriate base is usually present such as $Et_3N$ or pyridine although in some cases it is not necessary. Usually one equivalent of compound VIII (where R″=methyl) is employed. However, a large excess of compound VIII (where R″=H) is required in order to prevent bis-alkylation.

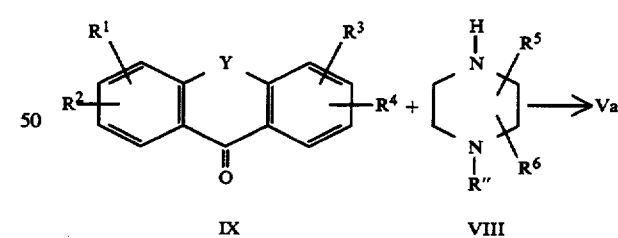

VII   VIII

An alternative mute for generating compound Va or IIa is by reductive amination of the dibenzoketone compound IX with the appropriately substituted piperazine VIII. The reaction is typically conducted in a polar solvent, such as ethanol, optionally in the presence of a dehydrating agent such as 3 Å molecular sieves. A variety of reducing agents can be employed, such as $NaCNBH_3$ or catalytic hydrogen utilizing for example $Pd/C/H_2$.

IX   VIII

Compounds VII and IX can be prepared following known methods including those methods set forth in the references above for the preparation of compounds IIa and Va. Scheme I below is a representative example for the preparation of IIa and Va.

The reaction is typically conducted in a polar solvent, such as ethanol, optionally in the presence of a dehydrating agent such as 3 Å molecular sieves. A variety of reducing agents can be employed, such as $NaCNBH_3$ or catalytic hydrogen utilizing for example $Pd/C/H_2$.

SCHEME I

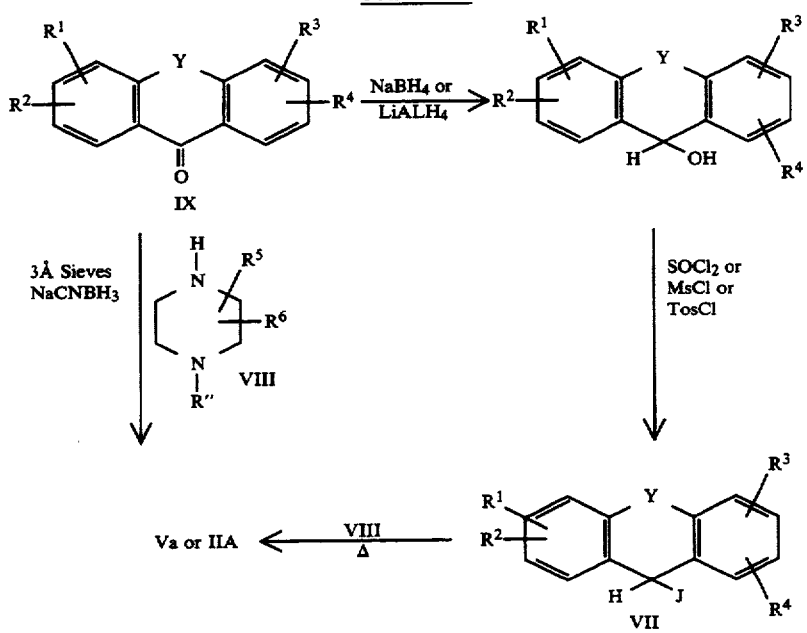

J = leaving group e.,g., halo, tosyl, mesyl.

PREPARATION OF DOUBLE BOND ANALOGS

Compounds of the formula Vb below, where T is a carbon atom having a double bond attached to the carbon atom of the dibenzo-tricyclic ring, may be prepared from Compound IX by the addition of the appropriately substituted Grignard or other metallated reagent, such as compound X below, to produce compound XI. The reaction usually is conducted in a dry aprotic solvent, such as THF, at a temperature ranging from about 0° C. to reflux. Dehydration of compound I with a suitable acid such as sulfuric acid or similar reagent will provide compounds of general formula Vb. The sequence in scheme XI below is a representative example for the preparation of Vb.

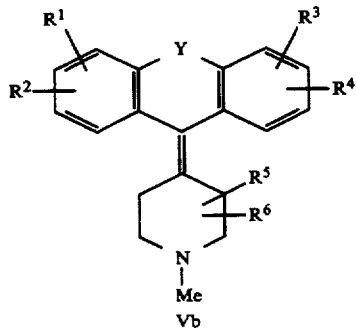

Scheme II

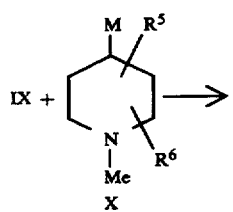

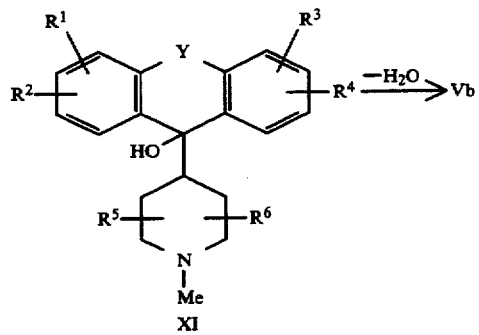

M is a metal such as Li or Mg.

The above procedure for producing compounds of general formula Vb is well-known in the literature. See, for example, Collect, Czech. Chem. Comm. 54(5), 1388-1402, (1989), J. Med. Chem. 17, 57 (1974), West German Patent No. 1670-334, and U.S. Pat. No. 4,021,561.

An alternative mute for generating compounds of formula Vb is by reacting the appropriately substituted compound of formula XII with the appropriately substituted compound of formula XIII to produce the carbinol XIV. The conditions for the addition may be the same as those described above.

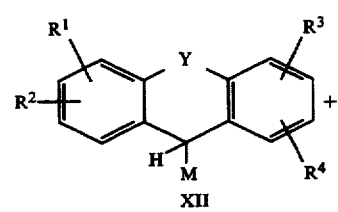

-continued

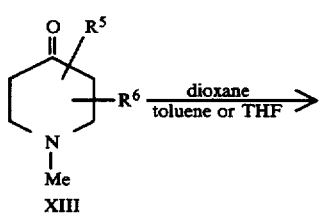

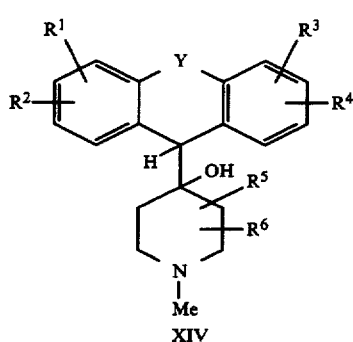

The intermediate XIV may then be dehydrated by converting it to the acyloxy compound, followed by pyrolysis at 200°-500° C. (See for example in West German Patent No. 1670-334). The reaction usually is conducted in an inert solvent such as dioxane, toluene or THF at −78° to 50° C.

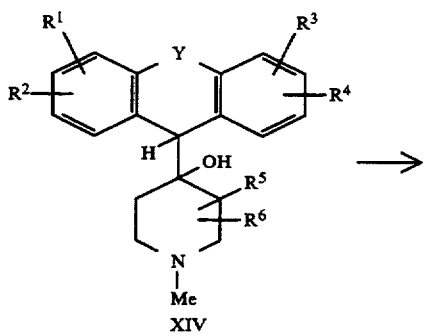

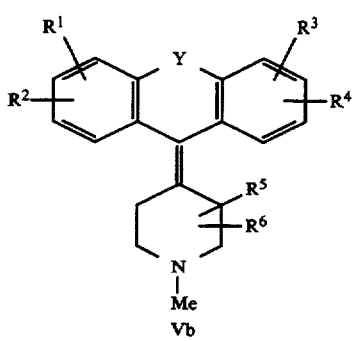

PREPARATION OF SINGLE BOND ANALOGS

Compounds of the general formula Vc below, where T is a carbon atom having a single bond attached to the carbon atom of the dibenzo-tricyclic ring, may be prepared via several methods.

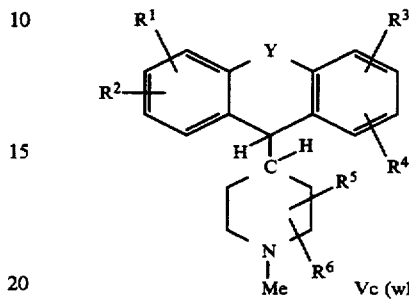

A. Treatment of compound VII where J is a leaving group, e.g. Br or Cl, with the appropriately substituted Grignard reagent X (or other corresponding metalated reagent M, e.g., organolithium) produces the desired compound of formula Vc.

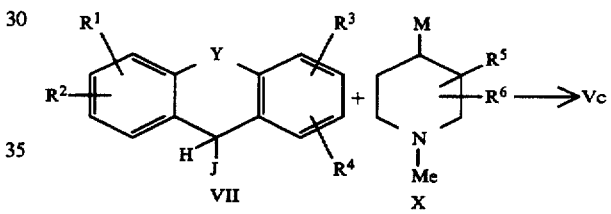

The reactions generally are conducted in an inert solvent such as ether, toluene, or THF at a temperature range of about −78° C. to +50° C.

Alternatively, the metalating substituent and the leaving group can be interchanged and reacted under the same conditions to produce the same compound of formula type Vc.

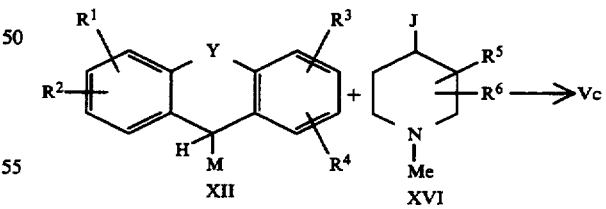

Further details on these processes are described in U.S. Pat. Nos. 3,419,565; 3,326,924:3.357,986 and *J. Org. Chem.* 50, 339 (1985).

B. Compounds of general formula type Vc may also be prepared by reductive removal of the hydroxyl group of the appropriately substituted compounds XI or XIV under a variety of conditions [e.g. the methods disclosed in *J.A.C.S.* 104 4976 (1982) and *J. Org. Chem*, 50, 339 (1985)].

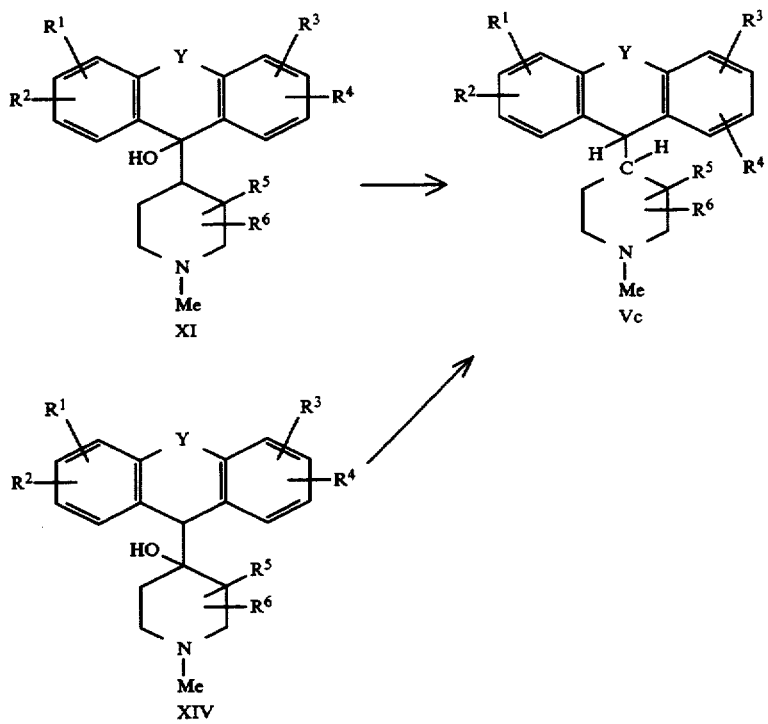

In some cases reductive removal of the hydroxy group of compound XI may also be accomplished by refluxing it with formic acid as described in *Tetrahedron Letters*, 29 (45) 5701-2 (1988) to produce compound Vc.

In the above processes, it is sometimes desirable and/or necessary to protect certain $R^1$, $R^2$, $R^3$, $R^4$, $R^5$, $R^6$, etc., groups during the reactions. Certain protecting groups have been described in the above processes but, as those skilled in the art will recognize, other protecting groups may be substituted. Conventional protecting groups are operable as described in Greene, T. W., "Protective Groups In Organic Synthesis," John Wiley & Sons, New York, 1981. For example, the groups listed in column 1 of Table 1 below may be protected as indicated in column 2 of the table:

TABLE 1

| PROTECTED GROUPS | |
|---|---|
| 1. GROUP TO BE PROTECTED | 2. PROTECTED GROUP |
| —COOH | —COOalkyl, —COObenzyl, —COOphenyl, —C(O/O/O)CH₃ |
| \NH/ | \NCOalkyl/, \NCObenzyl/, \NCOphenyl/ |
| \CO/ | (cyclic ketal structures) |

TABLE 1-continued

| PROTECTED GROUPS | |
|---|---|
| 1. GROUP TO BE PROTECTED | 2. PROTECTED GROUP |
| —OH | —O-(tetrahydropyranyl), —OCH₂phenyl, —OCH₃, OSi(CH₃)₂(t-Bu), |
| —NHR, wherein R is any substituent on an amino group within the scope of the claims | —N(R)-(tetrahydropyranyl), —NR—CO—CF₃, —NRCOCH₃, —NRCH₂phenyl |
| —NH₂ | —N(succinimide), —NH—C(O)—O(t-Bu) |

Other protecting groups well known in the art also may be used. After the reaction or reactions, the protecting groups may be removed by standard procedures.

The compounds of the invention possess platelet-activating factor ("PAF") and histamine antagonistic properties. They are, therefore, useful when PAF and/or histamine are factors in the disease or disorder. This includes allergic diseases such as asthma, allergic rhinitis, adult respiratory distress syndrome, urticaria and inflammatory diseases such as rheumatoid arthritis and osteo-arthritis. For example, PAF is an important mediator of such processes as platelet aggregation, smooth muscle contraction (especially in lung tissue), eosinophil chemotaxis, vascular permeability and neutrophil activation. Recent evidence implicates PAF as an underlying factor involved in airway hyperreactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vive test mimics clinical use of PAF antagonists to provide data which simulates clinical use of the compounds described herein.

A. IN VITRO STUDIES
PLATELET AGGREGATION ASSAY

Platelet-activating factor (PAF) causes aggregation of platelets by a receptor-mediated mechanism. Therefore, PAF-induced platelet aggregation provides a simple and convenient assay to screen compounds for PAF antagonism.

Human blood (50 ml) was collected from healthy male donors in an anticoagulant solution (5 ml) containing sodium citrate (3.8%) and dextrose (2%). Blood was centrifuged at 110×g for 15 min. and the supernatant platelet-rich plasma (PRP) carefully transferred into a polypropylene tube. Platelet-poor-plasma (PPP) was prepared by centrifuging PRP at 12,000×g for 2 min. (Beckman Microfuge B). PRP was used within 3 hr. of drawing the blood.

PAF was dissolved in chloroform:methanol (1:1, v/v) at a concentration of 2 mg/ml and stored at $-70°$ C. An aliquot of this solution was transferred to a polypropylene tube and dried under a flow of nitrogen gas. To the dried sample was added Hepes-saline-BSA (BSA=bovine serum albumen) buffer (25 mM Hepes, pH 7.4, 1254 mM NaCl, 0.7 mM $MgCl_2$ and 0.1% BSA) to obtain a 1 mM solution and sonicated for 5 min. in a bath sonicator. This stock solution was further diluted to appropriate concentrations in Hepes-saline-BSA buffer. Collagen (Sigma) and adenosine diphosphate (ADP) (Sigma) were purchased as solutions. Test compounds were initially dissolved in dimethyl sulfoxide (DMSO) at a concentration of 50 mM and then further diluted in Hepes-saline-BSA buffer to achieve appropriate concentrations.

When an aggregating agent such as PAF is added to PRP, platelets aggregate. An aggregometer quantifies this aggregation by measuring and comparing light (infra-red) transmission through PPP and PRP. Aggregation assays were performed using a dual-channel aggregometer (Model 440, Chrono-Log Corp., Havertown, Pa.). PRP (0.45 ml) in aggregometer cuvettes was continually stirred (37° C.). Solutions (50 $\mu$L) of test compounds or vehicle were added to the PRP and, after incubation for 2 min., 10–15 $\mu$l aliquots of PAF solution were added to achieve a final concentration of $1-5\times10^{-8}$M. In different experiments the aggregatory response was kept within a set limit by varying the concentration of PAF. Incubations were continued until the increase in light transmission reached a maximum (usually 2 min.). This increase in light transmission reflecting platelet aggregation is transmitted to a computer by the Chrono-Log model 810 AGGRO/LINK interface. The AGGRO/LINK calculates the slope of transmission change, thus providing the rate of aggregation. Values for inhibition were calculated by comparing rates of aggregation obtained in the absence-and the presence of the compound. For each experiment, a standard PAF antagonist such as 8-chloro-6,11-dihydro-11-(1-acetyl-4-piperidylidene)-5H-benzo[5,6]cyclohepta[1,2-b]pyridine was used as a positive control.

Compounds that inhibit PAF-induced aggregation were tested against several other aggregating agents including collagen (0.2 mg/ml) and ADP (2 $\mu$M). Compounds showing no activity against these latter agents were considered to be specific PAF antagonists. Results are shown in Table 2 below.

B. IN VIVO STUDIES: AGONIST-INDUCED RESPONSES
SPASMOGEN-INDUCED BRONCHOSPASM IN GUINEA PIGS

Male Hartley guinea pigs (450–550 g) were obtained from Charles River Breeding Laboratories. The animals were fasted overnight and the following day were anesthetized with 0.9 ml/kg i.p. of dialurethane (containing 0.1 g/ml diallylbarbituric acid, 0.4 g/ml ethylurea and 0.4 g/ml urethane). The left jugular vein was cannulated for the administration of compounds. The trachea was cannulated and the animals were ventilated by a rodent respirator at 55 strokes/min. with a stroke volume of 4 ml. A side arm to the tracheal cannula was connected to a pressure transducer to obtain a continuous measure of inflation pressure. Bronchoconstriction was measured as the percent increase in inflation pressure that peaked within 5 min. after challenge with spasmogen. The animals were challenged i.v. with either histamine (10 ug/kg), or PAF (0.4 $\mu$g/kg in isotonic saline containing 0.25% BSA). Each animal was challenged with only a single spasmogen. The effect of a compound on the bronchospasm is expressed as a percent inhibition of the increase in inflation pressure compared to the increase in a control group. Results are shown in Table 2 below for representative examples of compounds of the present invention. Compounds 1, 2 and 3 represent known compounds and are included for comparison purposes.

TABLE 2

| Compound No. | PAF Antagonism (in vitro) IC$_{50}$ (μM) | Agonist Bronchospasm (in vivo) - oral | | | |
|---|---|---|---|---|---|
| | | PAF | | Histamine | |
| | | Dose | % Inhibition | Dose | % Inhibition |
| 1 | 175 | 10 mg/kg | <50 | 1 mg/kg | >50 |
| 2 | 0.61 | 3 mg/kg | 4 | 3 mg/kg | 48 |
| 3 | 41 | | | | |
| 4 | 1.2 | 3 mg/kg | 82 | 3 mg/kg | 0 |

TABLE 2-continued

| Compound No. | | PAF Antagonism (in vitro) IC$_{50}$ (µM) | Agonist Bronchospasm (in vivo) - oral | | | |
|---|---|---|---|---|---|---|
| | | | PAF | | Histamine | |
| | | | Dose | % Inhibition | Dose | % Inhibition |
| 5 | 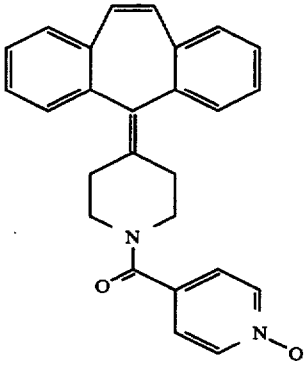 | 2 | | | | |
| 6 | 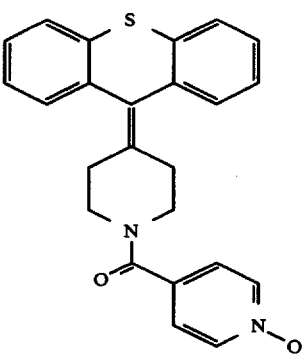 | 10 | | | | |
| 7 | 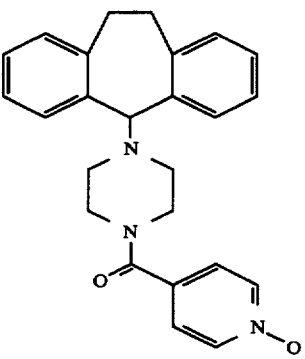 | 10 | | | | |
| 8 | 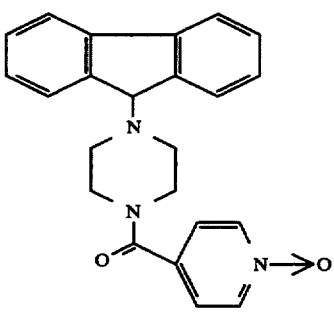 | 2.5 | | | | |

The compounds of structural formula I exhibit PAF antagonist and antihistaminic properties to varying degrees, i.e., certain compounds have strong PAF antagonistic activity, but have weaker antihistaminic activity. Other compounds are strong antihistamines but weaker PAF antagonists. Several of the compounds are both strong PAF antagonists and potent antihistamines. Consequently, it is within the scope of this invention to use each of these compounds when clinically appropriate. For example, if a strong PAF antagonist is required, but weaker antihistaminic activity is necessary, such a compound could be chosen by the clinician. Alternatively, if both potent PAF antagonism and antihistaminic activity are required, a different compound of the invention would be utilized by the clinician.

For preparing pharmaceutical compositions from the compounds described by this invention, inert, pharmaceutically acceptable carders can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be convened, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application. The appropriate dosage can be determined by comparing the activity of the compound with the activity of a known antihistaminic compound such as 8-chloro-6, 11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied, depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 1500 mg/day preferably 10 to 750 mg/day, in two to four divided doses to achieve relief of the symptoms. The compounds are believed to be non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

PREPARATIVE EXAMPLE

A.

4-(10,11-DIHYDRO-5H-DIBENZO[a,d]CYCLOHEPTEN-5-YLIDENE)-1-(2,2,2-TRICHLOROETHYLOXYCARBONYL)PIPERIDINE

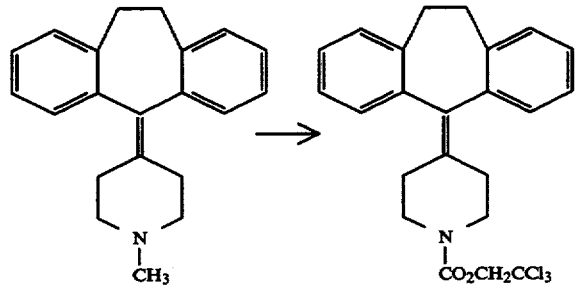

To a mixture of 4.35 g (15.1 mmol) of 1-(10,11-dihydro-5H-dibenzo[a,d]cyclohepten-5-ylidene)-4-methylpiperidine (J. Med. Chem. 8, 829, (1965)) and 3.0 mL of triethylamine in 80 mL of dry toluene at 90° C. and under an atmosphere of nitrogen was added over 40 min. 8.1 mL of 2,2,2,-trichlomethyloxycarbonyl chloride. The reaction mixture was then stirred for two hours. It was quenched with 1.0N aqueous sodium hydroxide and extracted with ether (3×). The combined organic portions were washed once each with 5% aqueous hydrochloric acid and brine. It was dried over magnesium sulfate, filtered, and concentrated in vacuo. The resultant oil solidified on standing to provide 6.3 g of the title compound.

B. 4-(10,11-DIHYDRO-5H-DIBENZO[a,d]CYCLOHEPTEN-5-YLIDENE)PIPERIDINE

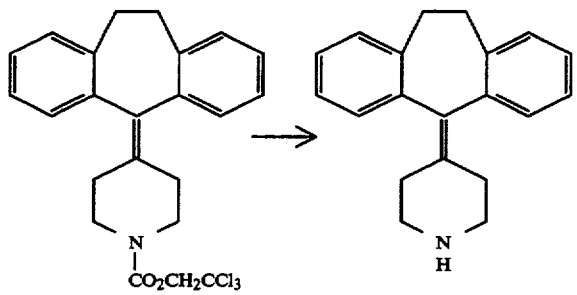

To a mixture of 6.3 g (18.2 mmol) of 1-(10,11-dihydro-5H-dibenzo[a,d]cyclohepten-5-ylidene)-4-(2,2,2-trichlomethyloxycarbonyl)piperidine in 100 mL of glacial acetic acid at 90° C. and under an atmosphere of nitrogen was added 12.36 g of zinc dust. After 3.5 hours, the reaction mixture was cooled and filtered. The filtrate was taken up in ethyl acetate and basified with aqueous sodium hydroxide. The organic phase was dried over magnesium sulfate, filtered and concentrated in vacuo. The crude product was recrystallized to give 2.23 g of the title compound as a white solid.

PREPARATIVE EXAMPLE 2

A. 1-(2,2,2-TRICHLOROETHYLOXYCARBONYL)-4-(9H-XANTHENE-9-YLIDENE)PIPERIDINE

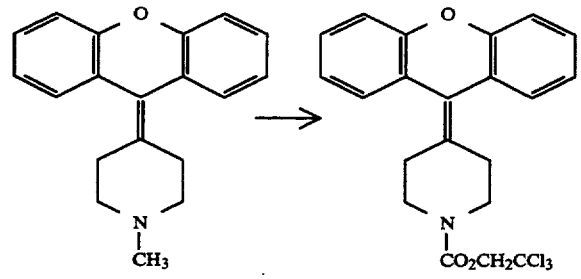

To a mixture of 430 mg (1.55 mmol) of 1-methyl-4-(9H-xanthene-9-ylidene)piperidine [*Tetrahedron Letters*, 29, 5701 (1988)] and 649 μL (4.65 mmol) of triethylamine in 20 mL of dry toluene at 85° C. under an atmosphere of argon was added over 10 min 1.06 mL (7.7 mmol) of 2,2,2-trichloroethyloxycarbonyl chloride. After 30 min the mixture was cooled to room temperature, poured into a solution of 25% aqueous sodium hydroxide, and was extracted with ethyl acetate (3×). The combined organic portions were dried over sodium sulfate, filtered, and concentrated with vacuo to afford the title compound as a crude oil.

B. 4-(9H-XANTHENE-9-YLIDENE)PIPERIDINE

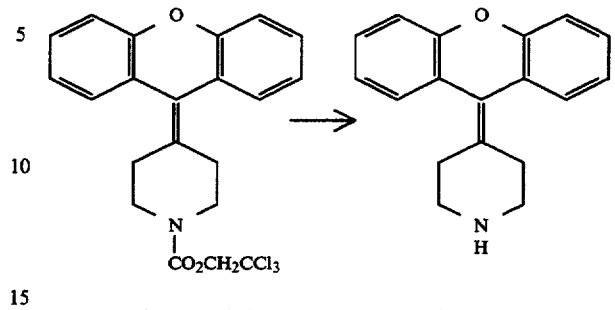

To a mixture of the crude product (above) in 20 mL of glacial acetic acid at 85° and under an atmosphere of argon was added 1.30 g (20 mmol) of zinc dust. After 30 min the mixture was filtered and concentrated in vacuo. The residue was diluted with water, washed with 1.0N aqueous sodium hydroxide, and extracted with methylene chloride. The combined organic portions were dried over sodium sulfate, filtered, and concentrated in vacuo. The residue was purified via flash chromotography (10% MeOH/CH$_2$Cl$_2$) to give 184 mg of the title compound as a glass.

PREPARATIVE EXAMPLE 3

5-PIPERAZINYL 10,11-DIHYDRO-5H-DIBENZO[a,d]CYCLOHEPTENE

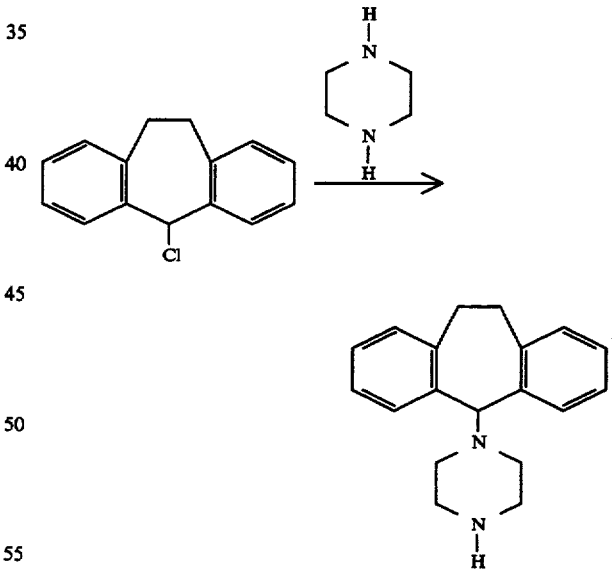

Into a solution of partially dissolved piperazine (15.2 g, 0.17 mmol) in THF (130 mL) at more temperature was added dropwise a solution of 5-chloro-10,11-dihydro-5H-dibenzo[a,d]cycloheptene (2.3g, 10.3 mmol) in 20 mL THF. The reaction was allowed to stir overnight and then was diluted with CH$_2$Cl$_2$, washed once with 1.0N NaOH solution, once with brine and then dried (Mg SO$_4$). It was then filtered and the solvent removed to give a residue which was flash chromatographed (5% MeOH saturated with NH$_3$ in CH$_2$Cl$_2$) to give 1.38 g of a glassy solid of the title compound.

PREPARATIVE EXAMPLE 4

A. 4-(9,10-DIHYDRO-10-METHYL-9-ACRIDINYL)-1-(2,2,2-TRICHLOROETHYLOXYCARBONYL)-PIPERIDINE

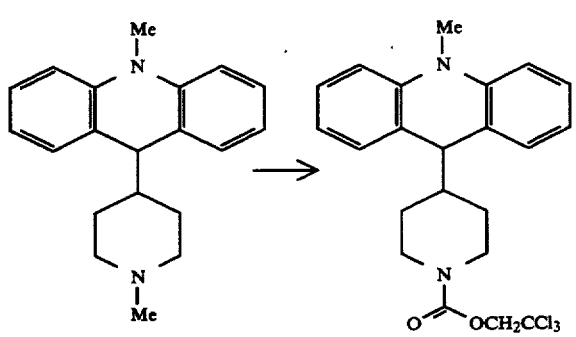

Trichloroethyl chloroformate (1.06 mL, 7.7 mmol) is added over a 10 minute period to a solution of 9,10-dihydro-10-methyl-9-(1-methyl-4-piperidinyl)acridine (453 mg, 1.55 mmol) [(*Tetrahedron Letters*, 29, 5701 (1988)] and triethylamine (649 µl, 4.65 mmol) in 20 mL of dry toluene at 85° C. The reaction is worked up after 30 minutes by extracting with EtOAc and washing with a 10% NaOH solution. The crude product is obtained after the solvent is removed.

B. 9,10-DIHYDRO-10-METHYL-9-(4-PIPERIDINYL)ACRIDINE

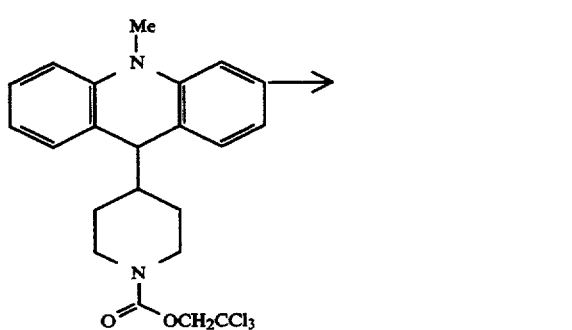

Zinc dust (1.3 g, 20 mmol) is added to a solution of the crude product from step A in 20 mL glacial acetic acid maintained at 85° C. The reaction mixture is filtered after 30 minutes and concentrated in vacuo. The residue is then diluted with water, basified with a 1.0N aqueous NaOH solution, and extracted with $CH_2Cl_2$. The extract is dried with $Na_2SO_4$, filtered and concentrated in vacuo. The residue is then purified via flash chromatography ($MeOH/CH_2Cl_2$) to provide the title compound.

PREPARATIVE EXAMPLE 5
4-(5,6,7,12-TETRAHYDRODIBENZO[a,d]CYCLOOCTEN)-12-YLIDENE PIPERIDINE

A. 5,6,7,12-TETRAHYDRO-12-(1-METHYL-4-PIPERIDINYL)DIBENZO[a,d]CYCLOOCTEN-12-OL

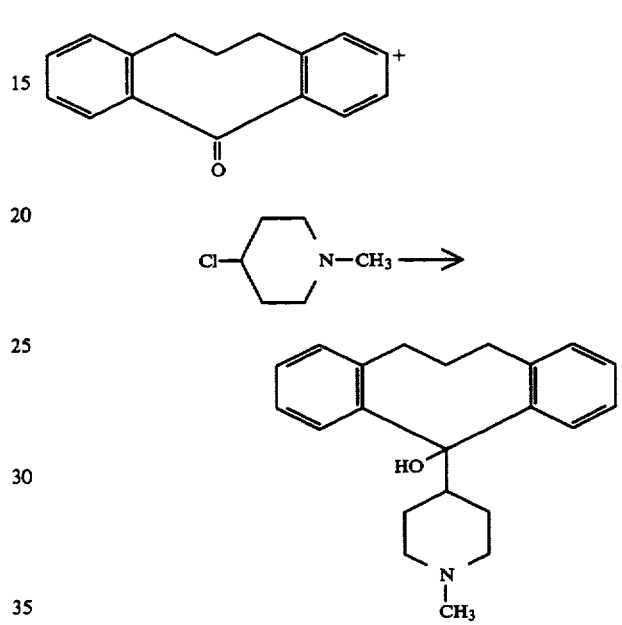

Sodium (2.7 g, 0.12 mol) is dissolved in $NH_3$ (200 ml) and the solution stirred for 20 minutes. 6,7-dihydrodibenzo[a,b]cycloocten-12-(5H)-one (13 g, 0.059 mol) [*Journal of Organic Chemistry* 52, 1549 (1987)] in THF (105 mL) is added slowly and the reactants stirred for 5 minutes. A solution of 4-chloro-1-methylpiperidine (7.8g, 0.058 mol) in THF (25 mL) is added with stirring. $NH_4Cl$ (5.0 g) and $NH_3$ (75 mL) are added and the stirring continued for an additional 2 hours. The mixture is concentrated to dryness then partitioned over water and EtOAc and extracted with additional EtOAc. The solvent then is removed to provide the compound.

B. 1-METHYL-4-(5,6,7,12-TETRAHYDRODIBENZO[a,d]CYCLOOCTEN-12-YLIDENE)PIPERIDINE

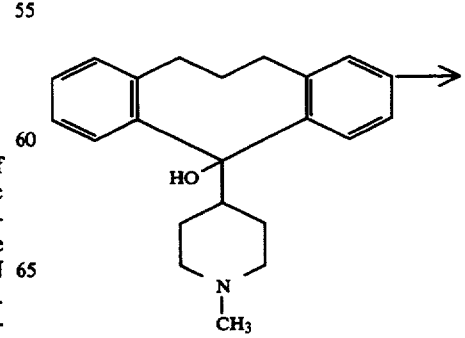

-continued

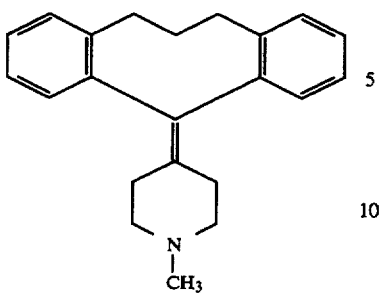

The title compound from part A above (1.4 g) is dehydrated with acetic acid (12 ml), acetyl chloride (7 ml) and acetic anhydride (3.5 ml) at 100° C. under a nitrogen atmosphere for 3 hours. The reaction mixture is then concentrated in vacuo and basified with sodium hydroxide (1N). After extraction with methylene chloride, the organic portions are dried with sodium sulfate. After filtration, the filtrate is evaporated to provide the title compound.

C. 2,2,2-TRICHLOROETHYL-4-(5,6,7,12-TETRAHYDRODIBENZO[a,d]CYCLOACTEN-12-YLIDENE-1-PIPERIDINE-CARBOXYLATE

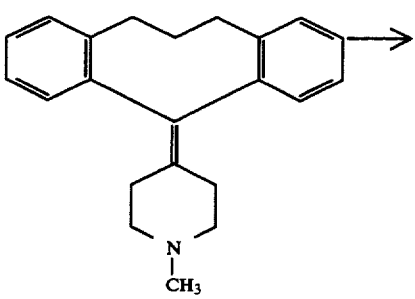

The title compound from part B above (1.003 g, 3.31 mol) is combined with triethylamine (0.70 mL) and dry toluene (30 mL) at 90° C. under an argon atmosphere. Trichloroethylchloroformate (1.60 mL) is added dropwise over a 20 minute period. The reaction is maintained at 90° C. for 20 hours, then cooled to room temperature and poured into aqueous NaOH (1N). The reaction mixture is extracted with CH$_2$Cl$_2$ (3×). The organic portions are combined, dried over Na$_2$SO$_4$, filtered and evaporated to dryness. The resulting fractions are purified by flash chromatography (2% CH$_3$OH in CH$_2$Cl$_2$) and combined to obtain the title compound.

D. 4-(5,6,7,12-TETRAHYDRODIBENZO[a,d]CYCLOOCTEN-12-YLIDENE)PIPERIDINE

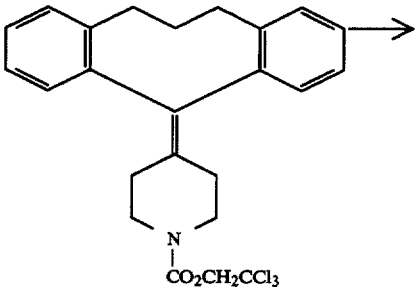

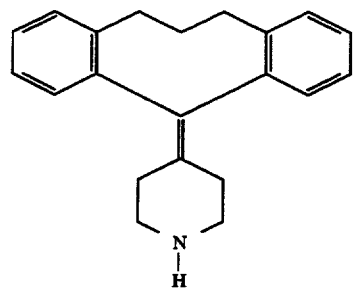

The title compound from part C above (1.0 g) is combined with glacial acetic acid (20 mL) and with zinc dust (2.12 g) under a nitrogen atmosphere at 90° C. After 3 hours, the reaction is cooled to room temperature, filtered and evaporated to dryness. The residue is basified with NaOH (1N) and extracted with CH$_2$Cl$_2$ (4×). The extracts are combined, dried over Na$_2$SO$_4$, filtered and evaporated to dryness. The compound fractions are purified by flash chromatography (5 to 7% CH$_3$OH/NH$_3$ in CH$_2$Cl$_2$) and combined to provide the title compound.

PREPARATIVE EXAMPLE 6

A. 9-CHLOROFLUORENE

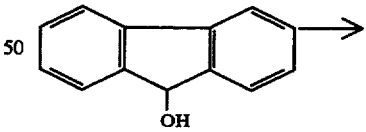

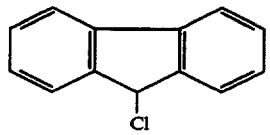

To a cold (0° C.) suspension of 9-hydroxyfluorene (49 g) in benzene (650 mL) was added thionylchloride (70 mL). This solution was allowed to stir while warming up to room temperature overnight. The benzene was distilled off and the product was recrystallized from isopropylether to give 41 g of the title compound as a white solid: m.p. 87°–89° C.

B. 1-(9H-FLUOREN-9-YL)-PIPERAZINE

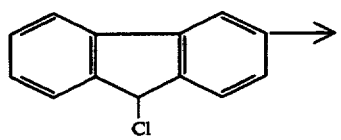

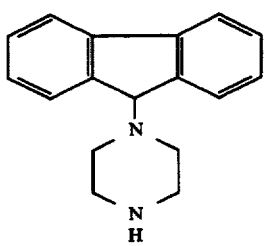

A solution of 9-chlorofluorene (8.4 g), triethylamine (0.85 mL) and piperazine (27 g) in THF (200 mL) was refluxed under argon for 6 hours. It was then filtered and the solvent was removed under vacuum. The crude product was washed with water, chromatographed on silica gel and eluted with 5% MeOH saturated with $NH_3$ in $CH_2Cl_2$ to afford the title compound (8.5 g).

PREPARATIVE EXAMPLE 7

A. 2,2,2-TRICHLOROETHYL-4-(9,10-DIHYDRO-10-METHYL-9-ACRIDINYLIDENE)-1-PIPERIDINECARBOXYLATE

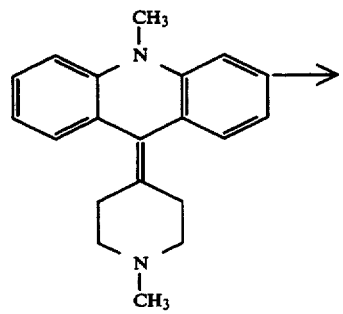

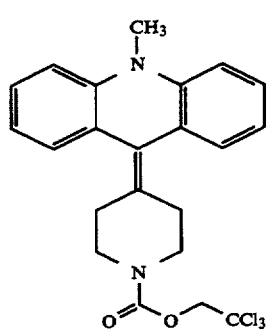

The above title compound was similarly prepared as in PREPARATIVE EXAMPLE 5, Procedure C to provide a solid: m.p. 189.5°–192° C. (recrystallized from MeCN).

B. 9,10-DIHYDRO-10-METHYL-9-(4-PIPERIDINYLIDENE)ACRIDINE

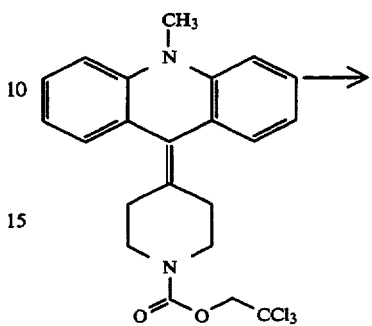

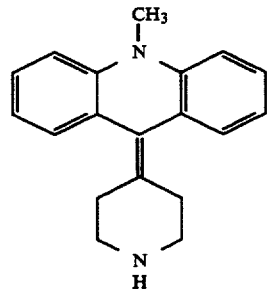

The above title compound was similarly prepared as in PREPARATIVE EXAMPLE 5, Procedure D as an oil after chromatography, eluted from silica gel by $CH_2Cl_2$—MeOH—$NH_4OH$ (97:2.7:0.3 by volume).

PREPARATIVE EXAMPLE 8

4-(6,10-DIHYDRODIBENZ[b,e]OXEPIN-10-YLIDENE)PIPERIDINE

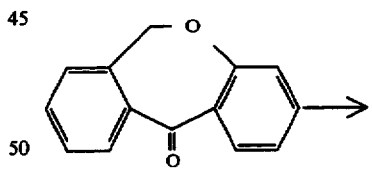

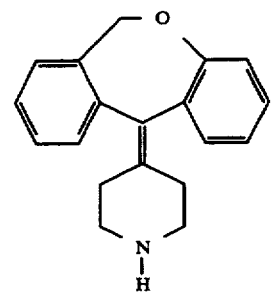

In a similar manner to that described in Preparative Example 5 steps A to D, the title compound is prepared from the ketone starting material shown above.

EXAMPLE 1

4-(5H-DIBENZO[a,d]CYCLOHEPTA-5-YLIDENE)-1-(4-PYRIDINYLCARBONYL)-PIPERIDINE N-OXIDE

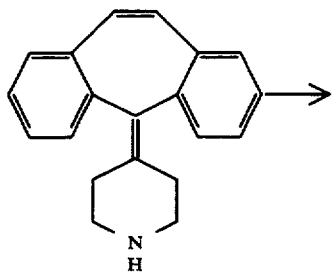

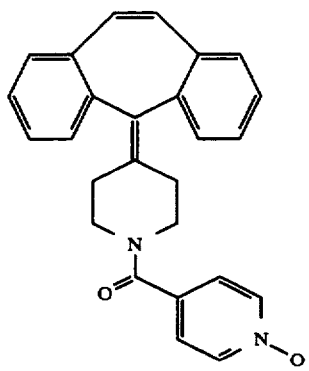

To a mixture of 442 mg (1.62 mmol) of 4-(5H-dibenzo[a,d]cyclohepta-5-ylidene)piperidine, (J. Med. Chem, 8, 829 (1965)) 234 mg (1.68 mmol) of isonicotinic acid N-oxide, and 274 mg (2.03 mmol) of 1-hydroxybenzotriazole hydrate in 5 mL of dry methylene chloride at −15° C. and under a nitrogen atmosphere was added dropwise a solution of 412 mg (16.9 mmol) of 1-(3-dimethylaminopropyl)-3-ethylcarbodiimide hydrochloride in 5 mL of dry methylene chloride. The reaction mixture was slowly allowed to warm to room temperature and was stirred overnight. It was poured into a solution of 10% aqueous sodium dihydrogen phosphate and extracted with ethyl acetate (3×). The combined organic portions were dried over $MgSO_4$, filtered, and concentrated in vacuo. The product was purified via flash chromatography (3% methanol saturated with ammonia in methylene chloride) and recrystallized (methylene chloride/isopropyl ether) to give 445 mg of the title compound as a white solid: mp 258°-260° C.; MS (FAB) m/z 395 ($M^+$ +1).

In a similar manner, the compounds of examples 2, 3, 4, 5, 8 and 9 in Table 3 below were prepared utilizing the indicated starting materials. In a similar manner the compounds of examples 6, 7, and 10 could be prepared from the indicated staring materials.

TABLE 3

| Example No. | Starting Compound | Final Product | Physical Properties |
|---|---|---|---|
| 2 | (structure) | (structure) | White Solid: mp 250-252° C.; MS(CI) m/z 397 ($M^+$ +1) |
| 3 | (structure) | (structure) | White Solid: mp 249-250° C.; MS(FAB) m/z 401 ($M^+$ +1) |

TABLE 3-continued

| Example No. | Starting Compound | Final Product | Physical Properties |
|---|---|---|---|
| 4 | (xanthene-piperidine structure) | (xanthene-piperidine with isonicotinoyl N-oxide) | Off-White Solid: mp 244–246° C. MS(FAB) m/z 385 (M⁺ +1) |
| 5 | (dibenzosuberane-piperazine structure) | (dibenzosuberane-piperazine with isonicotinoyl N-oxide) | mp 247–249° C.; MS (FAB) m/z 400 (M⁺ +1) |
| 6 | (N-methyl acridane-piperidine structure) | (N-methyl acridane-piperidine with isonicotinoyl N-oxide) | — |
| 7 | (dibenzocycloheptene-piperidine structure) | (dibenzocycloheptene-piperidine with isonicotinoyl N-oxide) | — |

TABLE 3-continued
| Example No. | Starting Compound | Final Product | Physical Properties |
|---|---|---|---|
| 8 | | | crystalline solid: m.p. 209–212° C. |
| 9 | | | oil, MS(EI) m/e 397.1774 (M+). |
| 10 | | | — |
EXAMPLE 11
4-(9H-THIOXANTHEN-9-YLIDENE)-1-4-(PYRIDINYLTHIOCARBONYL)PIPERIDINE
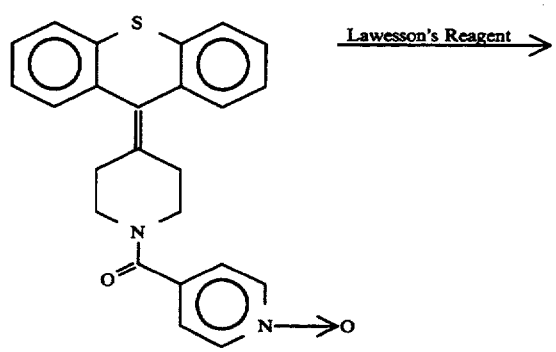
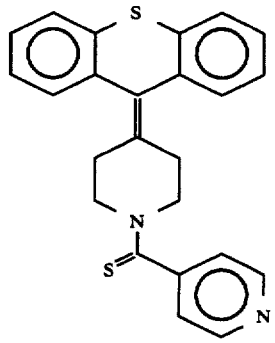
To a hot (75°–80° C.) suspension of 4-(9H-thioxanthen-9-ylidene)-1-(4-pyridinylcarbonyl)piperidine N-oxide (209 mg, 0.52 mmol) (Example 3) in toluene (10 ml) was added Lawesson's reagent (211 mg, 0.52 mmol). The reaction was allowed to stir at this temperature for 1 hr. It was then cooled and diluted with ETOAc (1.50 ml), washed once with H2O (150 ml), and once with brine (75 ml). After separation, the organic phase was dried (Na2SO4) and the solvent was removed to provide a crude product which was chromatographed on SiO2, (2.5% MeOH in CH2Cl2) to give 99 mg of the title compound as a yellowish solid: MS (El) m/e 400 (M+).

The following are examples of pharmaceutical dosage forms which contain a compound of the invention. As used herein, the term "active compound" is used to designate the compound:

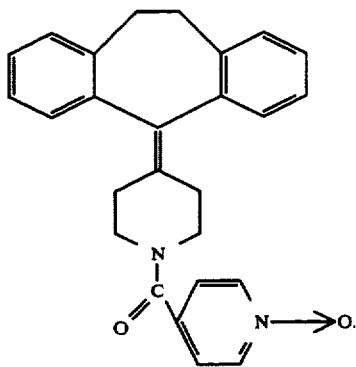

The scope of the invention in its pharmaceutical composition aspect is not to be limited by the examples provided, since any other compound of structural formula I can be substituted into the pharmaceutical composition examples.

PHARMACEUTICAL DOSAGE FORM EXAMPLES

EXAMPLE 12

| No. | Ingredients | Tablets mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

METHOD OF MANUFACTURE

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE 13

| No. | Ingredient | Capsules mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 250 | 700 |

METHOD OF MANUFACTURE

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula

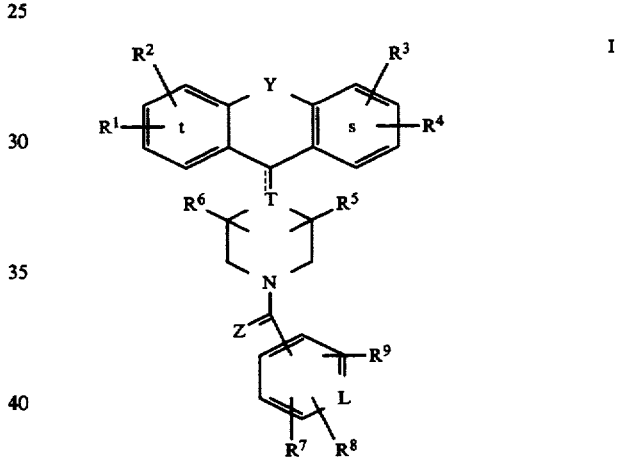

or a pharmaceutically acceptable salt or solvate thereof, wherein:

L represents N or $N^+O^-$;

Z represents O or S;

Y represents $-(C(R^a)_2)_m-X-(C(R^a)_2)_n-$ or

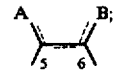

m and n are integers 0, 1, 2 or 3 such that the sum of m plus n equals 0 to 3;

when m plus n equals 1, X represents —O—, —S(O)$_e$— where e is 0, 1 or 2, —NR$^{14}$—, —C(O)NR$^{14}$—, —NR$^{14}$C(O)—, —C(S)NR$^{14}$—, —NR$^{14}$C(S)—, —CO$_2$— or —O$_2$C—, where R$^{14}$ is as defined below;

when m plus n equals 2, X represents —O—, —S(O)$_e$— where e is 0, 1 or 2, or —NR$^{14}$;

when m plus n equals 3, then X equals a direct bond;

when m plus n equals 0, X can be any substituent for m plus n equalling 1 and X can also be a direct bond, cyclopropylene or propenylene;

each R$^a$ may be the same or different and each independently represents H or $C_1$-$C_6$ lower alkyl;

the dotted line between the indicated carbon atoms 5 and 6 represents an optional double bond, such that when a double bond is present, A and B each independently represent —$R^{11}$, —$OR^{13}$, halo or —OC(O)$R^{11}$, and when no double bond is present between carbon atoms 5 and 6, A and B each independently represent H$_2$; —(OR$^{13}$)$_2$; (alkyl and H); (alkyl)$_2$; (—H and —OC(O)R$^{11}$), (H and —OR$^{11}$); =O or =NOR$^{14}$;

$R^1$, $R^2$, $R^3$, and $R^4$ may be the same or different and each independently represents H, halo, —CF$_3$, —OR$^{11}$, —C(=O)R$^{11}$, SR$^{11}$, —S(O)$_e$R$^{13}$ where e is 1 or 2, —N(R$^{11}$)$_2$, —NO$_2$, —OC(=O)R$^{11}$, —CO$_2$R$^{11}$, —OCO$_2$R$^{13}$, —NR$^{11}$C(=O)R$^{11}$, —CN, —CON(R$^{11}$)$_2$, alkyl, aryl, alkenyl or alkynyl, which alkyl group may be substituted with —OR$^{11}$, —SR$^{11}$, —N(R$^{11}$)$_2$ or —CO$_2$R$^{11}$ and which alkenyl group may be substituted with halo, —OR$^{13}$ or —CO$_2$R$^{11}$;

in addition, $R^1$ and $R^2$ may together form a benzene ring fused to the ring t and/or $R^3$ and $R^4$ may together form a benzene ring fused to the ring s;

$R^5$ and $R^6$ each independently represents H, alkyl or aryl, which alkyl may be substituted with —OR$^{11}$, —SR$^{11}$ or —N(R$^{11}$)$_2$;

in addition, $R^5$ may be combined with $R^6$ to represent =O or =S;

$R^7$, $R^8$ and $R^9$ each independently represents H, halo, —CF$_3$, —OR$^{11}$, —C(O)R$^{11}$, SR$^{11}$, —S(O)$_e$R$^{13}$ where e is 1 or 2, —N(R$^{11}$)$_2$, —NO$_2$, —CO$_2$R$^{11}$ OCO$_2$R$^{13}$, OCOR$^{11}$, —CN, —CON(R$^{11}$)$_2$, —NR$^{11}$COR$^{11}$, alkyl, aryl, alkenyl or alkynyl, which alkyl group may be substituted with —OR$^{11}$, —SR$^{11}$, —N(R$^{11}$)$_2$, or —CO$_2$R$^{11}$ and which alkenyl group may be substituted with halo, —OR$^{13}$ or —CO$_2$R$^{11}$;

each $R^{11}$ independently represents H, alkyl or aryl;
each $R^{13}$ independently represents alkyl or aryl;
each $R^{14}$ independently represents H or alkyl; and,
T represents

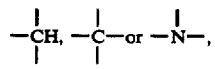

with the dotted line attached to T representing a double bond when T is C and being absent when T is

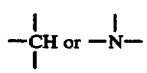

wherein:
alkyl—represents C$_1$-C$_6$ alkyl;
alkenyl—represents straight and branched carbon chains having at least one carbon to carbon double bond and containing from 2 to 12 carbon atoms, preferably from 3 to 6 carbon atoms;
alkynyl—represents straight and branched carbon chains having at least one carbon to carbon triple bond and containing from 2 to 12 carbon atoms, preferably from 2 to 6 carbon atoms;
aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_p$R$^a$ (wherein p is 0, 1 or 2 and R$^a$ is alkyl or aryl), —CF$_3$, amino, alkylamino, dialkylamino, —COOR$^{13}$ or —NO$_2$.

2. A compound according to claim 1, wherein Y represents

3. A compound according to claim 1, wherein Y represents —(C(R$^a$)$_2$)$_m$—X—(C(R$^a$)$_3$)$_n$—.

4. A compound according to claim 2, wherein the optional double bond between indicated carbon atoms 5 and 6 is absent.

5. A compound according to claim 2, wherein the optional double bond between indicated carbon atoms 5 and 6 is present.

6. A compound according to claim 4, wherein A and B each independently represent H$_2$; (alkyl and H); (alkyl)$_2$; (H and —OR$^{11}$); or =O.

7. A compound according to claim 3, wherein Y represents a direct bond, —X—, —CH$_2$—X—, —X—CH$_2$— or —(CH$_2$)$_3$—.

8. A compound according to claim 7, wherein X represents —O—, —S— or —NR$^{14}$.

9. A compound according to claim 1, wherein $R^5$ and $R^6$ each independently represent H or alkyl.

10. A compound according to claim 1, wherein $R^1$, $R^2$, $R^3$ and $R^4$ each independently represent H, alkyl, CF$_3$, halo, N(R$^{11}$)$_2$ or OR$^{11}$.

11. A compound according to claim 1, wherein $R^7$ and $R^8$ are both H and $R^9$ is as defined in claim 1.

12. A compound according to claim 11, wherein $R^9$ represents —H, —halo, —OR$^{11}$, —SR$^{11}$, —N(R$^{11}$)$_2$, or —alkyl.

13. A compound according to claim 1, wherein T represents

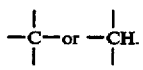

14. A compound according to claim 1, wherein T represents

15. A compound according to claim 1, wherein L is in the para position relative to the bond connnecting the pyridine ring to the rest of the compound.

16. A compound according to claim 1, wherein Z is O.

17. A compound represented by the structural formula

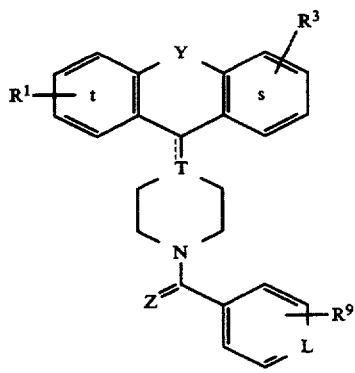

or a pharmaceutically acceptable salt or solvate thereof, wherein:

L represents N or N→O;
the dotted line represents an optional double bond;
Z represents O or S;
Y represents —CH=CH—, —CH$_2$—CH$_2$—, —X—, —CH$_2$, —X—, —X—CH$_2$— or —(CH$_2$)$_3$—, wherein X represents —O—, —S— or —NR$^{14}$;
R$^1$, R$^3$ and R$^9$ may be the same or different and each independently represents H, halo, —CF$_3$, —OR$^{11}$, —N(R$^{11}$)$_2$, alkyl, alkenyl or alkynyl; R$^9$ also may be SR$^{11}$;
R$^{11}$ represents H, alkyl or aryl;
R$^{14}$ represents H or alkyl; and
T represents

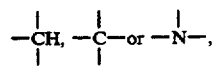

with the dotted line attached to T representing a double bond when T is

and being absent when T is

wherein:
alkyl—represents C$_1$-C$_6$ alkyl;
alkenyl—represents straight and branched carbon chains having at least one carbon to carbon double bond and containing from 2 to 12 carbon atoms, preferably from 3 to 6 carbon atoms;
alkynyl—represents straight and branched carbon chains having at least one carbon to carbon triple bond and containing from 2 to 12 carbon atoms, preferably from 2 to 6 carbon atoms;
aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more halo, alkyl, hydroxy, alkoxy, phenoxy, cyano, cycloalkyl, alkenyloxy, alkynyloxy, —SH, —S(O)$_p$R$^a$ (wherein p is 0, 1 or 2 and R$^a$ is alkyl or aryl), —CF$_3$, amino, alkylamino, dialkylamino, —COOR$^{13}$ or —NO$_2$.

18. A compound according to claim 17, wherein L represents N$^-$O$^+$.

19. A compound according to claim 17, wherein L represents N.

20. A compound according to claim 17, wherein Y represents —CH$_2$—CH$_2$—, —O—, —S—, —NR$^{14}$, —CH=CH—, —CH$_2$X—, or —X—CH$_2$—.

21. A compound according to claim 17 of the formula

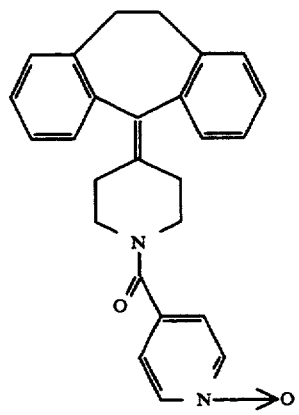

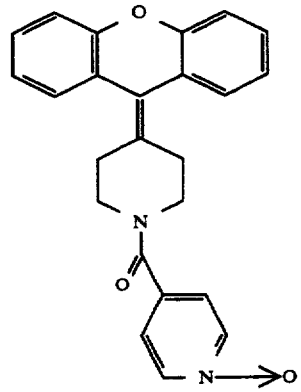

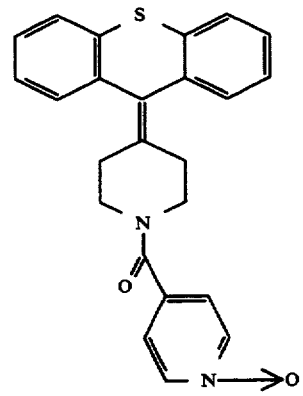

53
-continued
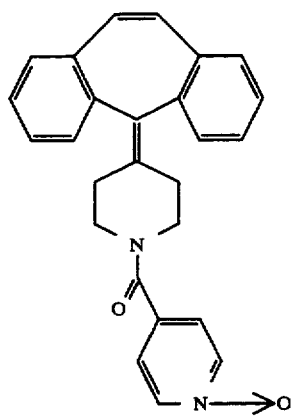
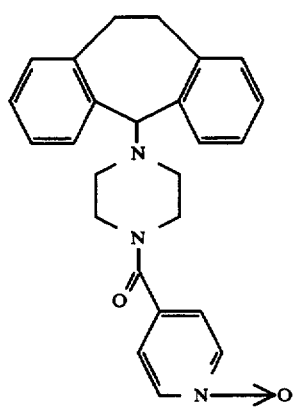
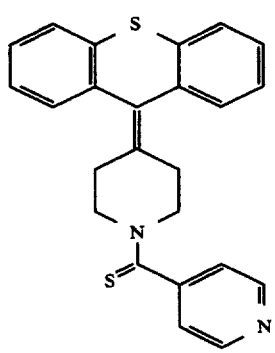
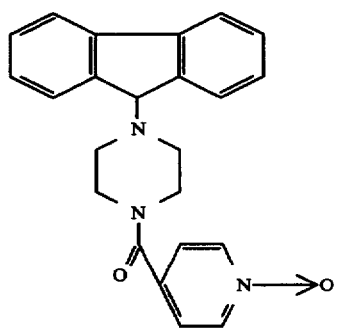
54
-continued
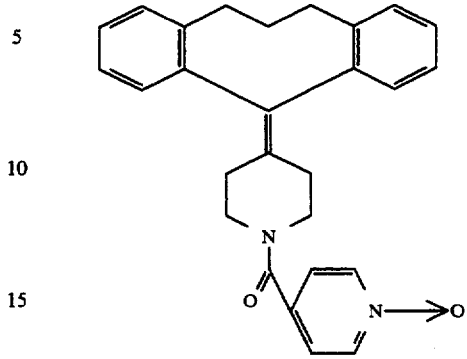
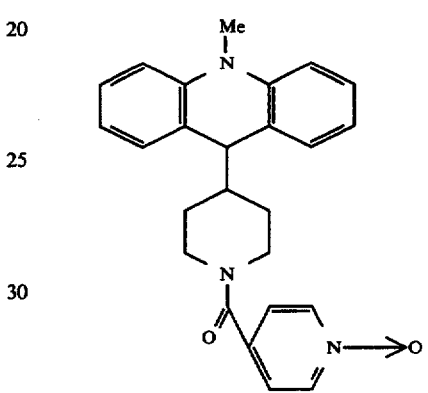
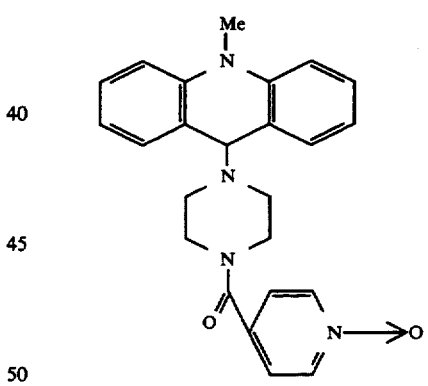
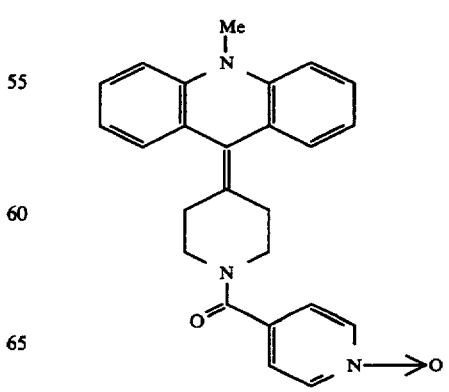

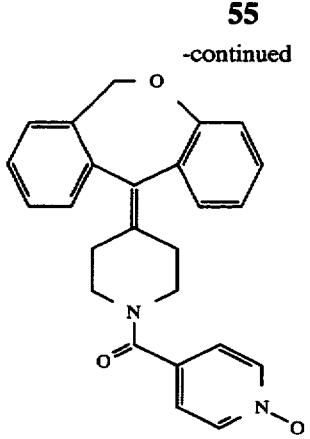

22. A pharmaceutical composition for treating allergic reaction and/or inflammation comprising a compound according to claim 1 in combination with a pharmaceutically acceptable carrier.

23. A method for treating allergic reaction in a mammal comprising administering to the mammal an antiallergic effective amount of a compound of claim 1.

24. A method for treating inflammation in a mammal comprising administering to the mammal an antiinflammatory effective amount of a compound of claim 1.

* * * * *